(12) United States Patent
Uhl et al.

(10) Patent No.: US 9,606,345 B2
(45) Date of Patent: Mar. 28, 2017

(54) MICROSCOPE DEVICE

(71) Applicants: FEI Company, Hillsboro, OR (US); TILL I.D. GMBH, Grafelfing (DE)

(72) Inventors: Rainer Uhl, Grafelfing (DE); Martin Schropp, München (DE)

(73) Assignee: FEI COMPANY, Hillsboro, OR (US)

( * ) Notice: Subject to any disclaimer, the term of this patent is extended or adjusted under 35 U.S.C. 154(b) by 75 days.

(21) Appl. No.: 14/346,906

(22) PCT Filed: Sep. 28, 2012

(86) PCT No.: PCT/US2012/058027
§ 371 (c)(1),
(2) Date: Mar. 24, 2014

(87) PCT Pub. No.: WO2013/049646
PCT Pub. Date: Apr. 4, 2013

(65) Prior Publication Data
US 2014/0313576 A1 Oct. 23, 2014

(30) Foreign Application Priority Data
Sep. 29, 2011 (DE) .......................... 10 2011 114 500

(51) Int. Cl.
*G02B 21/00* (2006.01)
*G02B 21/06* (2006.01)
(Continued)

(52) U.S. Cl.
CPC ......... *G02B 21/06* (2013.01); *G02B 21/0032* (2013.01); *G02B 21/14* (2013.01);
(Continued)

(58) Field of Classification Search
CPC .... G02B 21/00; G02B 21/0032; G02B 21/06; G02B 21/14; G02B 21/365; G02B 21/367;
(Continued)

(56) References Cited

U.S. PATENT DOCUMENTS 5,078,482 A * 1/1992 Feldman et al. ............... 359/371
5,381,224 A * 1/1995 Dixon et al. .................... 356/72
(Continued)

FOREIGN PATENT DOCUMENTS

DE 10330716 2/2005
DE 102007047465 4/2009
(Continued)

*Primary Examiner* — Stephone B Allen
*Assistant Examiner* — Adam W Booher
(74) *Attorney, Agent, or Firm* — Scheinberg & Associates, P.C.; Michael O. Scheinberg

(57) ABSTRACT

A microscope has an objective, a light source illuminating a sample over an illumination beam path, an arrangement producing a flat illumination pattern which is structured in both spatial directions on the sample, a surface detector detecting light coming over one picture beam path, an arrangement shifting the illumination pattern on the sample in one displacement direction, and a control unit taking one picture at a time of the light which was detected by the detector as phase picture in different positions of the pattern along the displacement direction and to computationally reconstruct from these phase pictures an overall picture of the illuminated sample region. The displacement direction is oblique to the main axes of symmetry of the illumination pattern and depending on the illumination pattern is chosen such that the number of phase pictures which is necessary for the picture reconstruction corresponds to the theoretically minimally required value.

27 Claims, 10 Drawing Sheets

(51) Int. Cl.
*G02B 21/14* (2006.01)
*G02B 21/36* (2006.01)
*G02B 27/58* (2006.01)
*G01N 21/64* (2006.01)

(52) U.S. Cl.
CPC ........... *G02B 21/367* (2013.01); *G02B 27/58* (2013.01); *G01N 21/6458* (2013.01)

(58) Field of Classification Search
CPC .... G02B 27/58; G01N 21/6458; G01B 11/25; G01B 11/2513; G01B 11/254
See application file for complete search history.

(56) References Cited

U.S. PATENT DOCUMENTS

| | | | |
|---|---|---|---|
| 5,751,417 A * | 5/1998 | Uhl | 356/318 |
| 6,731,383 B2 | 5/2004 | Watkins et al. | |
| 6,819,415 B2 | 11/2004 | Gerstner et al. | |
| 2005/0225849 A1* | 10/2005 | Gouch | 359/385 |
| 2008/0151206 A1* | 6/2008 | Baselmans et al. | 355/53 |
| 2009/0268280 A1 | 10/2009 | Osawa et al. | |
| 2010/0014088 A1* | 1/2010 | Wiki | 356/445 |
| 2010/0066823 A1* | 3/2010 | Westphal et al. | 348/79 |
| 2011/0025837 A1 | 2/2011 | Vossen et al. | |
| 2011/0109961 A1* | 5/2011 | Hayashi et al. | 359/385 |

FOREIGN PATENT DOCUMENTS

| | | |
|---|---|---|
| EP | 0507599 | 10/1997 |
| WO | 9845745 | 10/1998 |
| WO | 2008080032 A2 | 7/2008 |
| WO | 2008152605 A1 | 12/2008 |

* cited by examiner

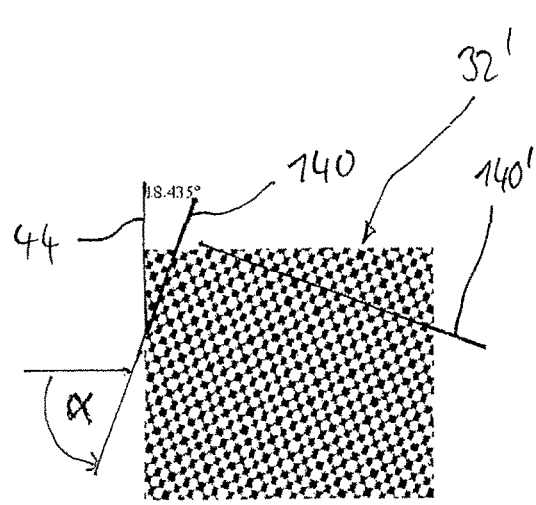
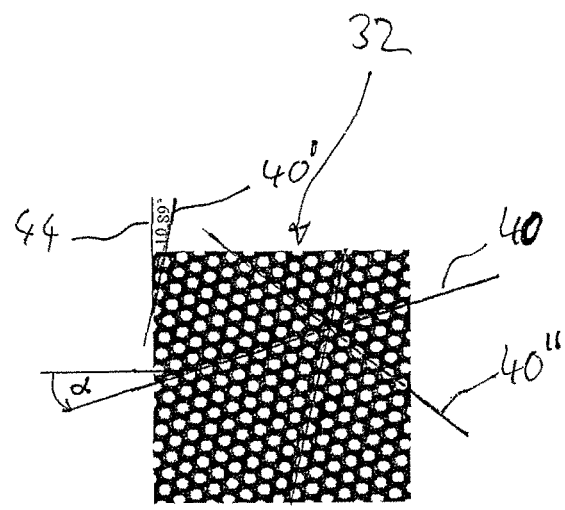
Fig. 2
Fig. 3

MICROSCOPE DEVICE

This invention relates to a microscope device with an objective, a light source for illuminating a sample, an arrangement for producing a structured illumination pattern on the sample, a detector for the light coming from the sample, an arrangement for displacing the illumination pattern on the sample and a control unit for taking pictures of the sample in different positions of the illumination pattern as phase pictures from which an overall picture of the illuminated sample region is computationally reconstructed.

Camera-based microscopic fluorescence (widefield) pictures suffer from the desired information from the focal plane being distorted by information from other planes of the preparation up to unrecognizablity.

To produce layer pictures in which the information can be viewed in isolation from a selected layer, conventionally confocal laser scanning methods are used in which the sample is scanned with one or more laser spots.

WO 92/14118 A1 discloses a microscope which using a surface sensor produces layer pictures computationally from individual pictures which have been taken with structured illumination. The individual pictures which are used for computation differ by the position of the projected structure on the preparation (these pictures are called "phase pictures" hereinafter). The illumination structure which is described in WO 92/14118 A1 is a two-dimensional checkered pattern which must be moved by exactly one half period in order to produce two phase pictures which are required for computation, exact imaging of the squares of the checkered pattern onto individual pixels being necessary so that the result reacts extremely critically to extremely small inaccuracies when the pattern is shifted. Moreover the sampling of a periodic signal (in this case the shifted pattern modulation) with only 2 points represents a violation of the Nyquist-Shannon sampling theorem; this leads to systematic and periodic evaluation errors (artifacts).

One more practicable version of the approach to computationally generating layer pictures from phase pictures which are produced at different positions of a pattern which has been projected onto the sample can be found in WO 98/45745 A1 and WO 02/12945 A2. Instead of a two-dimensionally structured illumination pattern one-dimensional ruled gratings are used there whose projection on the sample must be shifted at least twice in order to be able to compute the desired layer picture from three or more phase pictures.

In layer photographs which have been produced with the indicated procedure which is called "structured illumination", out-of-focus information is suppressed better than with a confocal laser scanning microscope. Moreover the method yields an increase in resolution in the direction which is perpendicular to the stroke orientation. This is used in the method which was described in the article "Doubling the lateral resolution of widefield fluorescence microscopy by structured illumination", M. G. L. Gustafsson, D. A. Agard, and J. W. Sedat, Proc. of SPIE 3919: 141-150, 2000, in which 3 times 3 phase pictures are recorded in which three grating positions at a time which have been generated by displacement are combined with three rotary positions at a time into grating preferential directions (0°, 120° and 240°). With respect to rotation, three orientations are sufficient, conversely translation can comprise instead of 3, also 5 or more positions. Thus layer pictures which no longer have a preferential direction with respect to the resolution which has been increased at maximum by a factor of 2 are computed from at least 9 phase pictures which are generated by linear translation and rotation.

EP 1 936 422 A1 describes a microscope with structured illumination in which the illumination pattern is produced by means of a ruled grating which is turned to take the phase pictures and is shifted in one direction perpendicular to the grating lines. The grating is also used for optical demodulation of the light originating from the sample. It is also mentioned that instead of a one-dimensional ruled grating also a two-dimensional grating can be used which must then be shifted in two directions perpendicular to the grating lines in order to take the phase pictures.

DE 10 2007 047 466 A1 describes a microscope with structured illumination in which by means of a ruled grating or a two-dimensionally structured grating an illumination pattern is generated which is shifted for taking phase pictures on the sample. By means of the grating a diffraction distribution in the pupil of the objective is produced which is then manipulated, for example by selection or rotation of the orders of diffraction, a structured phase plate being turned.

DE 10 2007 047 468 A1 discloses a microscope with structured illumination in which the sample is scanned by means of line-shaped illumination which is structured in the longitudinal direction, the scanning of the sample taking place several times with different phase positions, i.e. after shifting the line in the direction of structuring in order to produce different phase pictures which are balanced with one another. For purposes of sample scanning and phase shifting the illumination line is shifted by means of an X-Y scanner which is located between the illumination mask which has been illuminated by means of a cylindrical lens, and the tubular lens. The light coming from the sample likewise travels though the tubular lens before it is incident on a CCD detector. Between the light source and illumination mask there is a switchable attenuator in order to modulate the light intensity during scanning of the sample in the scanning direction. A "non-descanned" detection takes place on the CCD detector. The scanning of the sample is repeated several times, the line pattern on the detector being shifted for example by one line; this is achieved by a corresponding delay when the modulator is connected. In order to obtain a single phase picture, individual pictures which are generated by selection of certain lines and by "discarding" picture regions which are adjacent thereto must be added up. In this way a subsequently adjustable confocality is achieved.

DE 101 18 463 A1 and DE 101 55 002 A1 disclose microscope devices with structured illumination in which to obtain a phase picture a line focus which has been sinusoidally modulated in the longitudinal direction is projected onto the sample, and by shifting the line focus in the longitudinal direction different phase pictures are obtained which are subsequently balanced with one another. In order to increase the depth resolution there is a slotted diaphragm upstream of the detector. It is mentioned that the slotted diaphragm can be omitted when the detector is a CCD camera which views an intermediate picture plane.

DE 10 2007 009 550 B4 describes a microscope device for observing a moving sample which has been illuminated in a structured manner by means of a mask, a CCD chip being used as detector which is used as an adaptively variable diaphragm.

That the structured illumination microscope (SIM) has not yet been able to replace the confocal laserscanning microscope (CLSM) in spite of the indicated advantages in wide fields is due to two serious disadvantages of the method:

Taking several pictures which is necessary for producing a layer picture is less time-consuming than taking pictures by means of point scanner, but much more time-consuming than in a point pattern scanner (spinning disk). The disadvantage in speed compared to the latter is the more pronounced, the more phase pictures are necessary for the computation of a layer picture and the more operations which must be performed between the taking of individual phase pictures.

The thicker the sample and the more strongly it is colored, the less the brightness modulation caused by the pattern in the individual pictures. Thus the signal which is hidden in the modulation and which contains the desired layer information is masked by the background noise and disappears increasingly in noise. Accordingly the signal-to-noise ratio of the layer picture also suffers.

Therefore the object of this invention is to mitigate these disadvantages and to make available a durable device which could become the standard instrument for three-dimensional microscopy. This is achieved among others by minimizing the number of required phase pictures, by reducing the number of operations between phase pictures (instead of translation and rotation only translation), and by a series of measures which are suitable for increasing the modulation depth of individual phase pictures; this leads to layer pictures with improved signal-to-noise ratio.

This object is achieved as claimed in the invention by a microscope device according to claim 1 and a microscope device according to claim 6.

In the approach as claimed in the invention according to claim 1, it is advantageous that the number of required phase pictures can be minimized by a correspondingly chosen 2-dimensional illumination structure and a displacement direction of the flat illumination pattern relative to the sample which has advantageously been chosen for this purpose. This applies especially to the number of required operations between the individual phase pictures: instead of the translation and rotation which have been described in the prior art, only one translation is necessary.

The approach as claimed in the invention according to claim 6 is advantageous in that the illumination pattern does not acquire all sample regions at the same time, but is sequentially assembled and disassembled again on the sample and in doing so is recorded until the entire visual field has been acquired. At the same time all detector regions which are not being illuminated are switched to inactive. By this quasi-confocal detection of the pattern which is being assembled and disassembled again in sequence, effectively all scattered light which could reduce the modulated depth and thus the signal-to-noise ratio is masked out.

BRIEF DESCRIPTION OF THE DRAWINGS

Preferred configurations of the invention are given in the dependent claims.

The invention is detailed below by way of example using the attached drawings.

FIG. 2 shows a first example of an illumination pattern for use with this invention;

FIG. 3 shows a view like FIG. 2, but another example being shown;

FIG. 1 shows a first schematic example of a microscope device as claimed in the invention with structured illumination, a light source 10 for producing an illumination light beam 12, a microlens array 14, a beam deflection element 16, a first tubular lens 18 for the illumination light, a color divider 20, a microscope objective 22, a second tubular lens 26 for light emerging from a sample 24, and a camera detector 28 (for example CCD camera chip) being shown. The lens array 14 is located between the light source 10 and an intermediate picture plane 30 and is used to focus the excitation light beam 12 into the intermediate picture plane 30 such that a flat point pattern 31 is produced there which is structured in two directions of space. By means of the first tubular lens 18 and the objective 22 the point pattern 31 is imaged as structured illumination pattern 32 onto the sample 24, the color divider 20 being made reflective to the illumination light according to the example shown in FIG. 1. The light 34 which originates from the sample and which can be for example fluorescent light (the illumination light then acting as excitation light), is passed by the color divider 20 and imaged on the detector 28 by means of the objective 22 and the second tubular lens 26.

Figure 1:
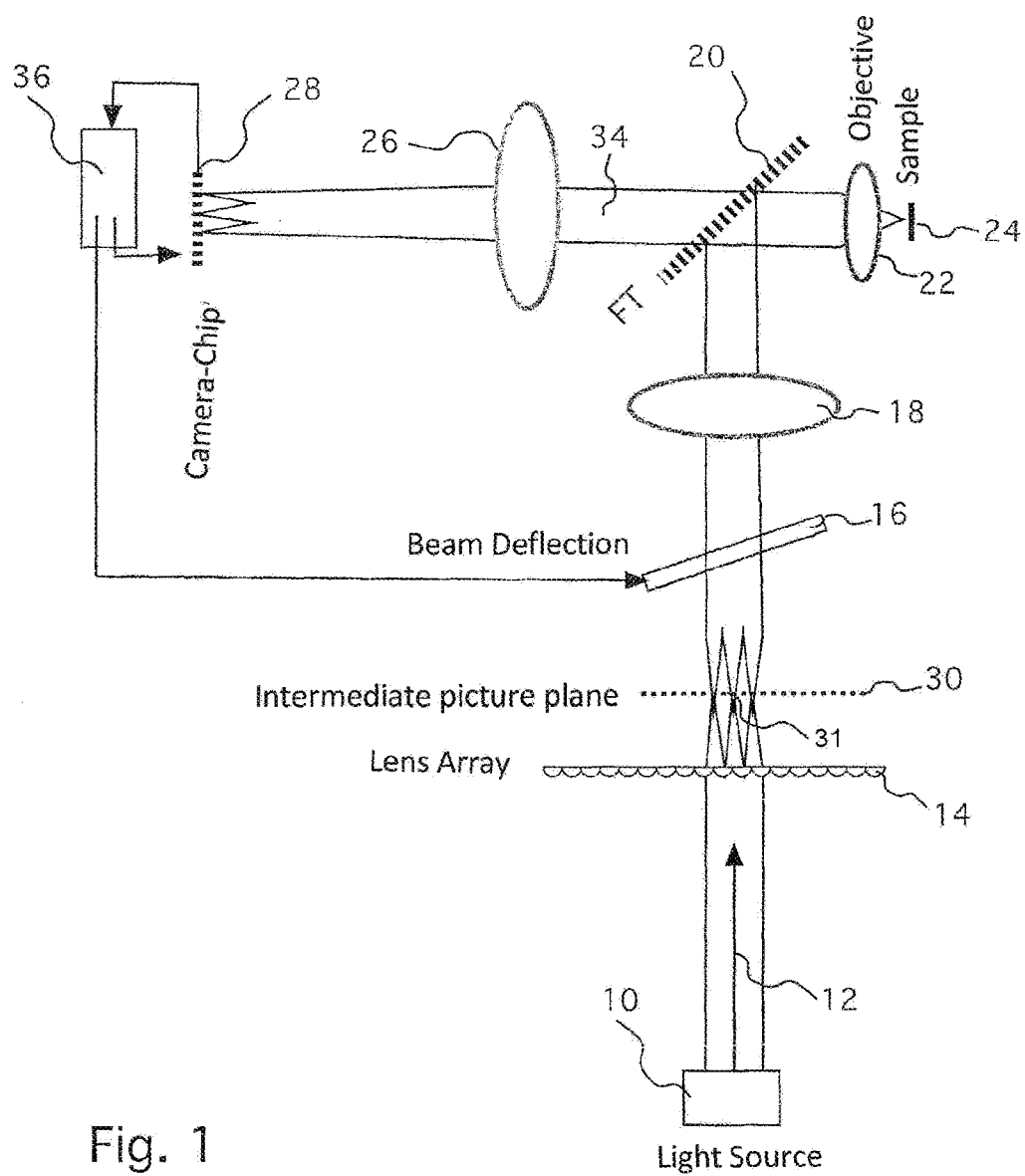
FIG. 1 shows one schematic example of a microscope device as claimed in the invention.

By means of the beam deflection element 16 the illumination pattern 32 can be shifted relative to the sample 24 in order to record different phase pictures, i.e. pictures with different phase angle of the three-dimensionally structured illumination pattern with respect to the sample 24. A control unit 36 synchronizes the beam deflection element 16 which is necessary for generating the phase shift with the picture-taking by the camera 28 and thus causes the taking of phase pictures which can be balanced with one another in order to obtain the desired layer picture of the sample.

The arrangement which is shown in FIG. 1 with the microscope lens array 14 is especially suitable for excitation with laser light, i.e. coherent light, and alternatively for producing the pattern by a microlens array upstream of the intermediate picture plane 30 a perforated mask array (not shown) can be placed in the indicated intermediate picture plane 30. But this reduces the radiant efficiency accordingly. A third possibility which works exclusively with coherent light will be described below.

In the embodiment which is shown in FIG. 1, the beam deflection element 16 is located in a non-infinite space between the intermediate picture plane 30 and the first tubular lens 18. The beam deflection element 16 can be for example a motorized deflection mirror or a pivotally mounted glass window. The former influences not only the position of the pattern on the sample, but also the pupil beam, the latter conversely leaves the pupil beam unchanged, because the beam offset of the illumination beam 12 which has been effected does not change its angle. Since to produce the different phase pictures however only a relatively small shift of the illumination pattern 32 on the sample 24 is necessary (on the order of magnitude of the illumination light wavelength), the beam offset in the pupil of the objective can be kept negligibly small by a suitable placement of a beam deflection element 16 which is made as a deflection mirror. In order to achieve the same thing when the beam deflection element 16 is placed between tubular lens 18 and objective 22, the beam deflection element 16 would have to be placed near the pupil of the objective.

In the method as claimed in the invention, excitation is carried out with a three-dimensionally modulated excitation light pattern, and the remaining three-dimensional modulation of the light which has been emitted from the sample is evaluated. In order to achieve modulation as great as possible, the number of critical optical elements in the beam path which could reduce the modulation depth should be reduced to the minimum. This succeeds best when the illumination pattern arises only in the object plane or—where this is not possible—in a plane which is conjugated to the plane of the picture so that the imaging errors can be compensated to the maximum degree.

While in the example shown in FIG. 1 the projection of a flat pattern which has been produced in the intermediate image plane 30 onto the sample 24 is used, alternatively the desired structuring of the illumination light can also be produced only in the sample 24 itself, by means of interfering focal points of coherent illumination light from the pupil of the objective. For example, the interference from the coherent light which originates from seven hexagonally arranged points in the pupil of the objective in the sample plane 24 (i.e. the other focal plane of the objective 22) produces a blanket hexagonal illumination pattern 32 (see FIG. 3). A suitable phase plate can be inserted into the intermediate image plane 30 to produce these seven points in the pupil of the objective for a telecentric optical structure.

The displacement of the illumination pattern which is necessary for taking different phase pictures on the sample 24 can then take place, besides by a beam deflection element 16 which was described above, also by a suitable relative phase shift of the amplitudes of the focal points and the pupil of the objective. The focal points can be assigned to the orders of diffraction of the illumination pattern, the relative phase shift of the focal points corresponding exactly to the relative phase shift of the Fourier orders of the illumination pattern on the sample 24. The phase shift can for example be produced by a galvanometric scanner in or near the pupil of the objective, an acousto-optical modulator or also by directly influencing the optical path in the infinite beam path (when it is made for example as interferometer with a combination of a piezoelectric actuator and a mirror in one arm of the interferometer).

The generation of the desired illumination pattern by interference in the sample also allows a high-resolution version of total internal reflection fluorescence microscopy (TIRFM). Since the local frequency of the illumination pattern which has been produced by interferometry depends on the relative distance of the focal points to one another, by choosing this frequency near the resolution boundary, i.e. by positioning the focal points on the edge of the pupil, with suitable objects a total reflection of the individual interfering beam components can be achieved at the transition from the cover glass to the sample. This allows TIRF excitation with increased surface resolution. When the interference pattern in the sample is produced, it must however be considered that TIRF is only ensured when only 6 points from the pupil of the objective in the sample are caused to interfere. In the procedure described farther above for producing a hexagonal pattern in the pupil of the objective using a phase plate, six hexagonally arranged points with one point in the center which originates from the zero order of diffraction of the interference result there by diffraction. If this zero order of diffraction were not suppressed, a considerable background would result which ruins a TIRF measurement. For this reason it is advantageous to produce the 6 focal points which are necessary for interference in the sample 24 in the pupil of the objective "farther forward" in the illumination beam path 12. This then also enables a variable matching of the TIRF angle.

In the embodiment shown in FIG. 1 for each phase picture all regions of the sample surface to be illuminated are illuminated at the same time with the illumination pattern, i.e. the microlens array 14 (or, in the alternative embodiments the point mask or phase mask) is fully illuminated by the illumination light beam 12 over a large area. Typically the surface to be optically stimulated will be rectangular, and the surface is to be optically stimulated as uniformly as possible.

The illumination pattern is preferably a hexagonal point pattern since a hexagonal pattern on the one hand delivers a three-dimensionally more homogeneous resolution increase in the picture plane after balancing the phase pictures than for example a checkered point pattern (with a hexagonal pattern a resolution increase just as large is achieved as with the grating which has been turned three times and which is described in the initially mentioned article by Gustafsson et al.) and on the other hand also has a fill factor which is smaller by a factor of 1.5 than a line pattern or checkered pattern. Due to the fill factor the unwanted background and thus the noise contribution from unwanted focal planes are reduced. Fundamentally, by illuminating a sample with a three-dimensionally structured illumination pattern and by subsequent evaluation of several phase pictures not only a layer photograph with removal of unwanted out-of-focus information is generated, but also a horizontal resolution increase in the pertinent picture plane is achieved when several phase pictures are taken in which the pattern is shifted with respect to the sample in order to change the three-dimensional phase of the illumination pattern, and these phase pictures are then balanced with one another in a suitable manner. In doing so a resolution increase by a factor of 2 can be achieved at maximum per direction of space, i.e. the diffraction-induced resolution boundary of the microscope can thus be exceeded at maximum by a factor of 2 (a description of this effect can be found for example in the initially cited article by Gustafsson et al.). For the practical application of this principle it is desirable to optimize the motion which is necessary for obtaining the phase pictures between sample and illumination pattern with respect to the number of required phase pictures and the simplicity of the required movements.

According to one aspect of this invention, it has been recognized that with a skillful choice of the angle of the displacement direction of the pattern relative to the main axes of symmetry of the pattern it is possible to achieve layer photographs with maximum resolution increase by sole displacement of the pattern along this displacement direction with some few phase pictures which have been taken along this displacement direction. Here the displacement direction is chosen depending on the illumination pattern such that the number of phase pictures which are necessary for picture reconstruction corresponds to the value which is theoretically the minimum required for the number of frequency orders of the illumination pattern which have been taken into account (i.e. the number of Fourier orders of the illumination pattern which have been recombined in the origination of the picture). In the frequency space this corresponds to the criterion that for the chosen displacement direction each of the frequency orders under consideration from one phase picture to the next undergoes a phase shift as explicit as possible in the sense that the phase shift of each frequency order differs as much as possible from the phase shift of the other frequency orders, i.e. each frequency order is shifted so to speak with its own speed.

First the important results of the detailed mathematical derivation which follows in Sections 1 to 3 are summarized.

FIG. 3 shows as an example a hexagonal point pattern as illumination pattern in which the angle α of the displacement direction 42 with respect to one of three equivalent main symmetry directions (labeled 40 in FIG. 3) is ±19.11° or n*60°±19.11° (n=1, 2, 3, . . . ) when only the first frequency orders of the illumination pattern are taken into account (based on the hexagonal symmetry with the three equivalent main symmetry directions here, there are three first orders; for a checkered pattern there are accordingly only two first orders); in FIG. 3 the angle of the direction which is labeled 44 and which is perpendicular to the displacement direction 42 is shown with the main axis of symmetry 40' which is accordingly 10.89°; the third main direction of symmetry is labeled 40" in FIG. 3. As is stated in Section 2.3, for the first orders there it still a second solution, specifically 10.9°; for practical reasons (smaller necessary absolute displacement and better fault tolerance) however the first solution is preferred. Preferably the displacement direction 42 in practice should be chosen such that this angle α is in the range between 18.6 and 19.6°.

FIG. 2 shows a checkered pattern as illumination pattern, here the theoretically optimum angle α between the displacement direction 42 and the main axis of symmetry 140 being 71.565° when only the first frequency orders of the illumination pattern are taken into account (the other main axis of symmetry is labeled 140' in FIG. 2). Fundamentally the angle here can be n*90°±71.565° (according to section 2.2 here there is also a second theoretical solution which however in practice is less favorable for the reasons which were named for the hexagon). But generally a hexagonal pattern is preferred due to the higher symmetry and of the smaller fill factor.

In consideration of only the first frequency orders of the illumination pattern, in the case of a hexagonal pattern at least seven different phase pictures along the displacement direction 42 must be taken, while in the case of the checkered pattern five different phase pictures are sufficient.

The results for the consideration of higher orders for a hexagonal illumination pattern are shown in section 2.5 and especially in Table 1. Accordingly for example the optimum displacement angle with consideration of the first and second orders of the pattern is 13.90° (the second solution, 5.21°, is less advantageous), 13 different phase pictures being necessary for complete picture reconstruction. With consideration of the first, second and third orders of the pattern, the optimum displacement angle is 6.59°, then 19 different phase pictures being necessary for complete picture reconstruction. Table 1 also shows that the selected displacement angle for a hexagonal illumination pattern in practice should be selected to be in the range from 1° to 20°, preferably 4 to 20 degrees (since the $\Theta_1$ solutions are better suited), the exact value depending on the number of Fourier orders of the illumination pattern which are to be considered in the respective application. In most cases the consideration of the first orders or of the first and second orders will be sufficient so that the chosen displacement angle will generally be between 13 and 20°.

For the hexagonal illumination the fill factor is smaller than for checkered illumination and each illuminated field is surrounded in all directions by unilluminated regions, as a result of which the modulation of the individual phase pictures is amplified and the noise contribution from unwanted focal planes which is to be eliminated in the balancing of the phase pictures is reduced.

The respective phases for the different phase pictures are preferably uniformly distributed over the region of the possible phase angles. The displacement of the pattern which is necessary for the individual phase pictures is on the order of magnitude of the wavelength of the excitation light (typically the three-dimensional structuring of the illumination pattern is in the vicinity of the diffraction boundary and thus on the order of magnitude of the wavelength of the excitation light). Since the required displacement of the illumination pattern is thus very small, an arrangement of the beam deflection element 16 in the noninfinite space, as shown in FIG. 1, is not critical.

The noise contribution from other than the desired focal plane can be further reduced according to one aspect of the invention in that the illumination pattern is not applied and recorded at the same time at all sites of the sample, but is assembled and disassembled again sequentially on the sample until the entire visual field has been acquired. For each phase field therefore the illumination pattern in partial regions of the sample surface to be illuminated is assembled and disassembled again, the partial regions altogether covering the sample surface which is to be illuminated. Each phase picture accordingly originates not by simultaneous illumination of the entire sample surface, but sequentially by partial illumination with the illumination pattern. In doing so the detector 28 is triggered such that essentially only the detector region 137 is active at the time onto which the just illuminated partial region of the sample surface is imaged. The detector itself is thus used as quasi-confocal slotted diaphragm. The technique which is known from another connection for taking a camera picture by recording with a defined slot width is also called "rolling shutter" technique.

Figure 5:
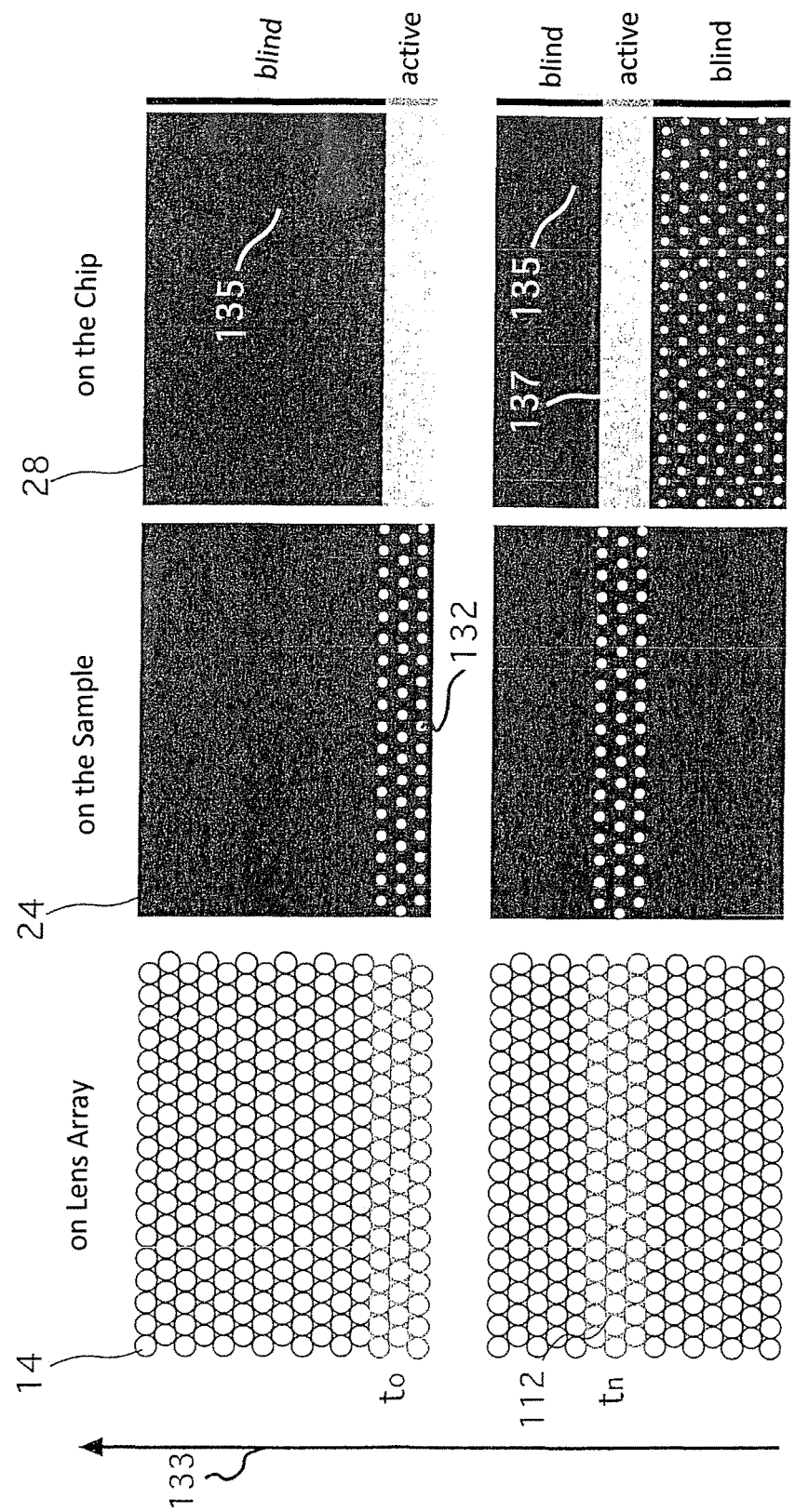
FIG. 5 shows an illustration of the sequential assembly and disassembly of the illumination pattern on the microlens array, the sample and the camera chip.

Advantageously the illumination pattern is assembled and disassembled in the form of a strip which migrates in the same direction as the "rolling shutter" moves. This is illustrated in FIG. 5 using a hexagonal pattern where in the upper part at time $t_0$ the location of an illumination light strip 112 on the microlens array 14 which is made with hexagonal symmetry (on the left in FIG. 5), the location of a strip 132 of the hexagonally structured illumination pattern resulting therefrom on the sample 24 (middle in FIG. 5), and the location of the strip-shaped image 137 of the sample region illuminated by the strip 132 on the camera chip 28 (on the right in FIG. 5; the region 137 also corresponds to the part of the camera chip which has been actively switched at time $t_0$) are shown; in the lower part of FIG. 5 the respective location of the strip 112, 132 and 137 at time $t_n$ is shown, the direction in which the strips 112, 132 and 137 migrate being labeled 133 in FIG. 5. The part of the detector 28 which is not active at the respective instant is indicated in FIG. 5 by means of a gray area which is labeled 135.

The narrower the illuminated and detected strip 132 in the direction 133, the more the arrangement approaches an arrangement which is confocal into one direction, in the boundary case its being a strip confocal microscope ("slit scan confocal"). If the width of the strip 132 is chosen such that it corresponds to the height of the camera chip 28, this corresponds to the case described above with reference to FIGS. 1 to 3 with an illumination pattern which is stationary during the taking of a phase picture. The narrower the strip 132 is selected to be, the better signal contributions on unwanted focal planes are suppressed, as a result of which the modulation depth is increased and the signal/noise ratio is improved. But at the same time the exposure time thus becomes shorter and the individual pattern points must be made correspondingly brighter in order to achieve a given signal/noise ratio. Since however sample damage increases more with the peak intensity than with the applied light dose, the sample damage due to the excitation light likewise increases with increasing confocality. To prevent sample damage longer measurement times or a poorer signal to noise ratio must be tolerated. In the former case, instead of moving the illumination strip 132 more slowly over the sample, several phase pictures will be taken in one strip position and the average formed therefrom. By varying the width of the illumination strip the compromise which is best at the time between signal/noise ratio, picture-taking rate and sample damage can be chosen.

When using a hexagonal pattern (as is shown in FIG. 5), with a three-line illumination strip 132 (as is shown in FIG. 5) the theoretically maximally possible resolution increase can be achieved, in any case it can be useful for avoiding artifacts to design the active detection gap width on the camera chip 28 to be somewhat smaller or somewhat larger than would correspond exactly to this strip width.

This procedure combines structured illumination with a descanned confocal detection on the camera chip 28 (in contrast for example to the method which was described in DE 10 2007 047 468 A1). In contrast for example to the method which was described in DE 10 2007 047 468 A1, it is not necessary either to modulate the intensity of the illumination light during the sequential assembly and disassembly of the illumination pattern over time, there is no "feedthrough" from one position of the illumination strip to the next, and at the end of the single scan process there is already a complete phase picture which uses all lines of the detector chip, no subsequent confocal correction of the picture being necessary.

The practical advantages of the proposed method will be briefly explained using a sCMOS chip. In its rolling shutter mode the chip can read out 1080 lines in 10 ms. This is 10 microseconds/pixel/line. If an "Airy Disk" is projected onto 8 pixel lines, to one hexagonal elementary cell there belong 24 pixel lines whose readout lasts 222 microseconds. The taking of a phase picture thus lasts 10,222 ms. If for return of the beam a maximum 768 µs are estimated, which is realistic, the taking of one phase picture lasts 11 ms and the taking of all phase pictures which are necessary for a high-resolution layer picture last 7 times as long, i.e. 77 ms. Accordingly, in principle 13 layer pictures/second are obtained, at a picture size of 2540×1080 pixels. A confocal microscope for this purpose requires many times longer for this purpose and at the same time loads the sample dramatically more. By reducing the size of the field, correspondingly higher photography rates can be achieved without increasing the sample loading.

Figure 4:
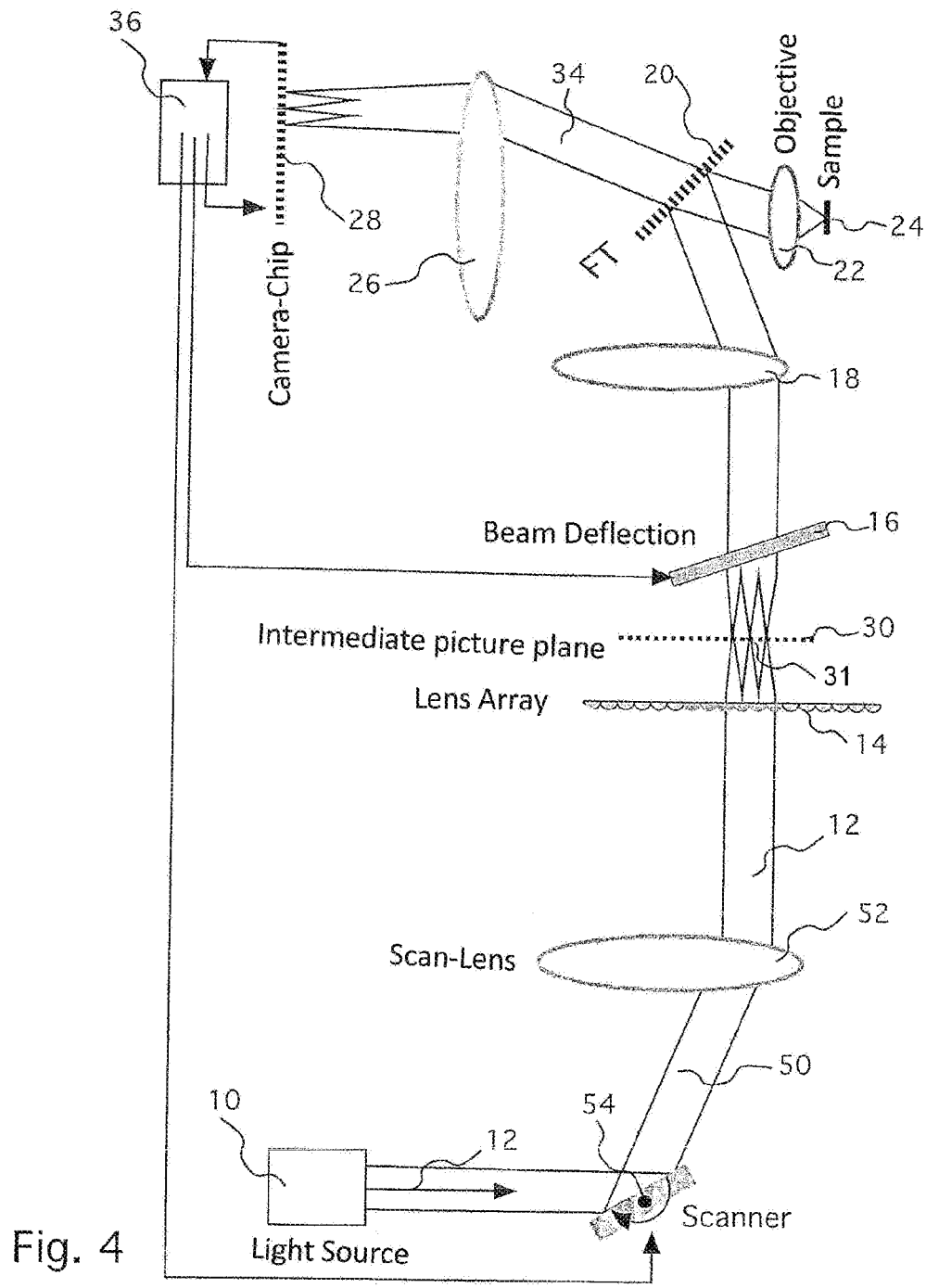
FIG. 4 shows a view like FIG. 1, one alternative example of a microscope device as claimed in the invention being shown which is especially suitable for a sequential illumination of the sample.

FIG. 4 schematically shows a microscope device with which the described sequential structured illumination of the sample can be implemented. In contrast to the structure according to FIG. 1, between the light source 10 and the microscope array 14 there are a scan device 50, a scan lens 52 and a motorized scanner mirror 54 to move the laser beam 12 which is used to illuminate the lens array 14 over the microlens array 14 such that it is sequentially illuminated in the form of a strip 112 which migrates in the direction 133. In doing so, in the intermediate picture plane 30 a correspondingly migrating illuminated strip of the point pattern is formed which is imaged accordingly onto the sample 24 by means of a first tubular lens 18 and the object 22 so that a correspondingly migrating strip 132 of the illumination pattern which is sequentially assembled and disassembled forms. Since for the movement of the illumination strip 132 on the sample much larger paths are necessary than in the displacement of the illumination light pattern which is necessary to obtain different phase pictures on the sample, for this purpose a special scan device 50 must be provided which—viewed from the light source 10—is located in front of the intermediate picture plane 30 in a plane which is conjugated to the pupil of the objective so that during scanning, the beam position in the pupil of the objective remains constant. The scan device 50 here moves only the noncritical illumination strip 132 (by its moving the light strip 112 over the microlens array 14), but not the extraordinarily critically modulated illumination light whose modulation depth would critically deteriorate in passage through scan optics. Any loss of modulation depth would moreover specifically degrade the modulation depth of the phase picture. In the structure as shown in FIG. 4, these problems are avoided by the modulated illumination picture being produced only in a plane which is absolutely symmetrical to the camera picture, as a result of which all errors of the optical system are compensated. Analogously to the statements made above, instead of a microlens array 14, in front of the intermediate image plane 30 a perforated mask array (not shown) or a phase plate (likewise not shown) can be introduced in the intermediate picture plane 30 itself. The beam deflection which is necessary for producing the phase pictures takes place, exactly as described above, for example using a beam deflection element 16.

As in the example from FIG. 1, preferably one pattern with hexagonal symmetry is used, as a result of which the resolution in the sample plane can be maximized. In doing so, also in the example from FIG. 4, as in the example from FIG. 1, instead of a lens array 14 a corresponding perforated mask in the intermediate picture plane 30 could be used.

If the intention is to achieve higher picture rates with abandonment of maximum resolution increase, instead of a hexagonal pattern a strip pattern can be produced as illumination pattern on the sample and scanned in the manner described with reference to FIGS. 4 and 5 with respect to a hexagonal pattern, sequentially and with masking-out of all emissions from sample regions which have not just been illuminated (descanned detection). In this aspect of the invention the illumination pattern which forms on the sample sequentially for one phase picture at a time is structured only in one direction of space, i.e. in the longitudinal direction of the illumination strip, while in the direction perpendicular thereto, i.e. the direction 133 of the sequential assembly and disassembly of the illumination pattern, there is no three-dimensional structuring. This arises only on the detector by the synchronized movement of the "rolling shutter".

Here an optimized compromise between sample damage on one side (the wider the strip, the smaller the intensity becomes with which the sample is locally illuminated) and improvement of the signal/noise ratio can be established by increasing the modulation depth over the selected width of the illumination strip 132.

Figure 6A:
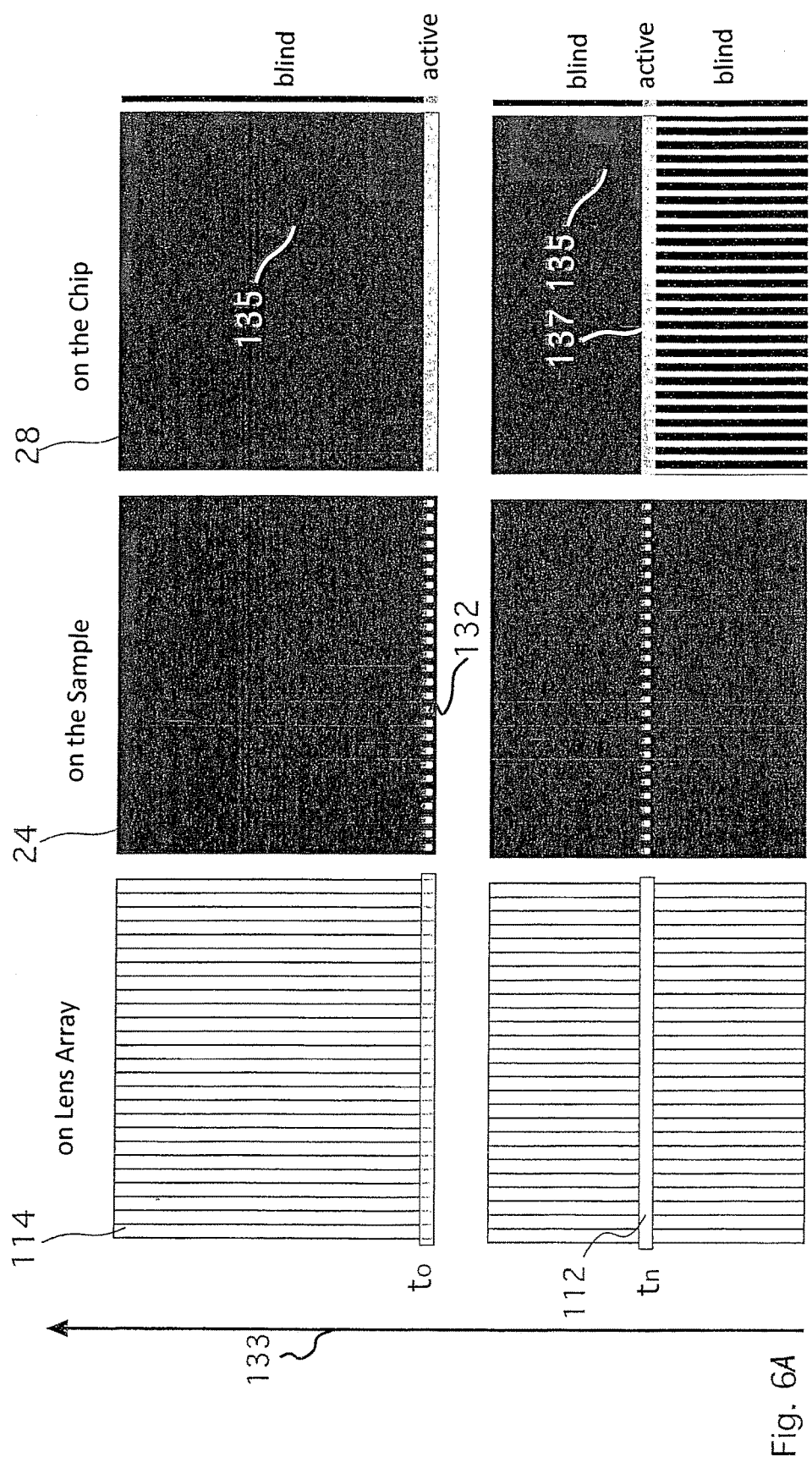
FIGS. 6A and 6B show views like FIG. 5, but two different modified embodiments with cylindrical lens arrays being shown.

FIG. 6A shows a boundary case in which only one strip 132 which is diffraction-limited in height is illuminated, as a result of which the advantages of a "slit confocal" structure are combined with those of a structure with structured strip illumination.

For generating a strip pattern, for example as shown in FIG. 6A, a cylindrical lens array 114 can be used, the axial direction of the lenses coinciding with the direction 133 in which the illumination strip 132 is assembled and disassembled by the illumination light beam strip 112 being moved over the cylindrical lens array 114 by means of the scan device 50. Alternatively a strip mask can be used in the intermediate picture plane 30, whose strips run parallel to the direction 133. When using a cylindrical lens array 114 however the radiant efficiency is (almost) twice as high. By omitting the cylindrical lens array (or the grating) a classical slotted mask confocal microscope is obtained. Its depth resolution is less than that of an arrangement as claimed in the invention, but only a single scan and not three of them is needed to take the picture.

A further measure which is suitable for minimizing information from all planes which lie outside the desired focal plane and in this way for achieving a maximum modulation depth and an optimum signal/noise ratio, exists in the generation of the desired illumination pattern in the sample by means of multiphoton excitation. In doing so the known layer sensitivity of multiphoton excitation is used, as a result of the nonlinearity of the multiphoton excitation essentially only in the desired focal plane a fluorescence excitation of the sample taking place. Thus a maximum modulation excitation of the light is achieved still deep in the sample, and in the computational evaluation of the phase pictures only still scattered emission light from other planes of the sample must be removed.

A blanket, i.e. extending over the entire camera chip, point pattern would distribute the laser output among too many points, and as a result of the quadratic intensity dependency of the excitation, would make unrealistically high laser outputs necessary. Therefore it is advantageous to concentrate the laser output as described above only on a narrow strip 132 and to guide it over the sample surface to be illuminated as a point pattern which is sequentially assembled and disassembled. The resulting fluorescent light is detected parallel thereto in the described manner sequentially and selectively on the region 137 of the camera chip 28, which region is actively switched at the time. Twice (or for three-photon excitation, triple) the excitation wavelength does provide for poorer resolution, but the method is aimed predominantly at good contrast, high speed and low photon loading of the sample. Accordingly, the illumination mode which is described in FIG. 6A is especially well suited for a multiphoton excitation.

Figure 6B:
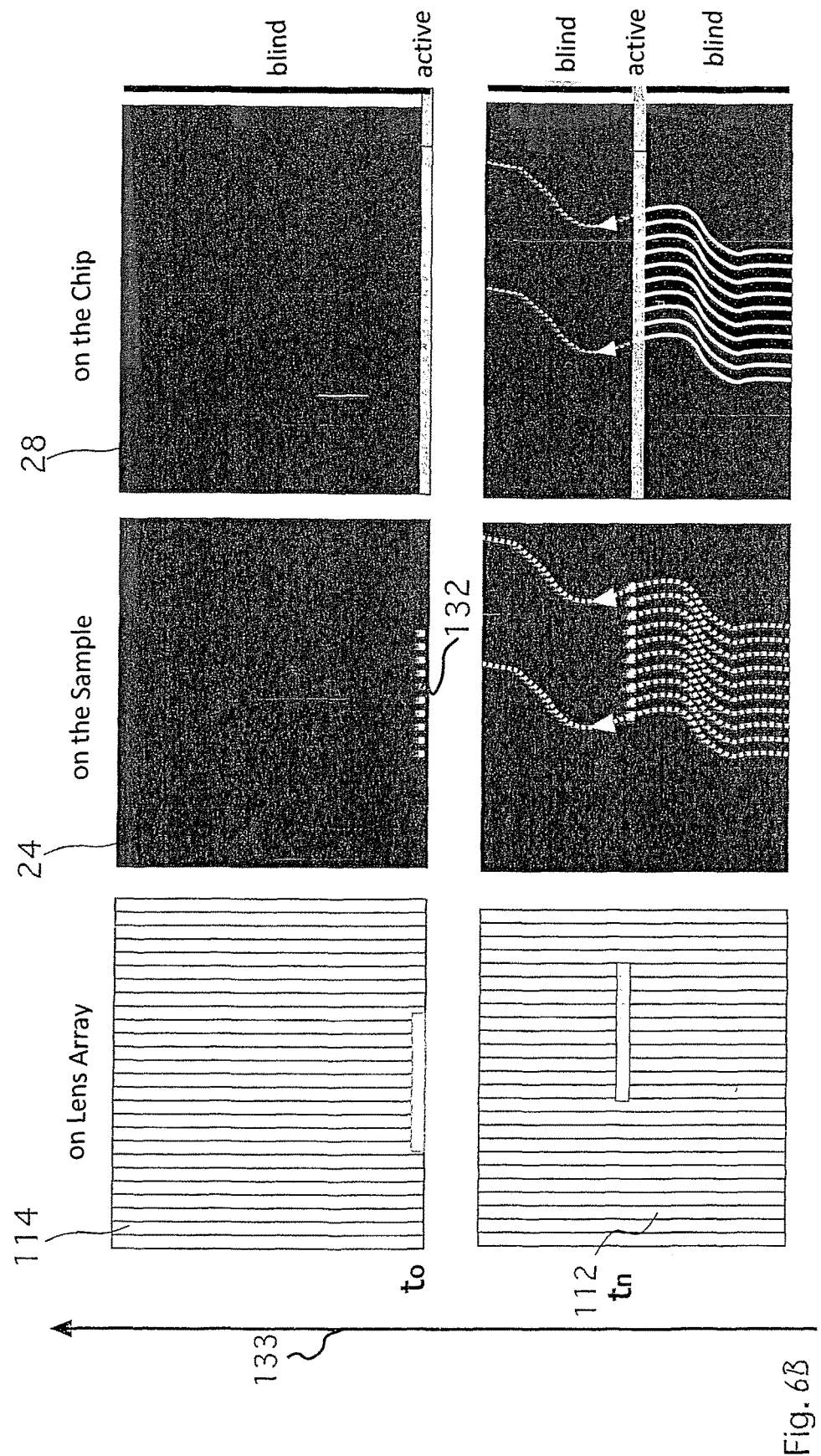

If the luminance of a sensor-wide strip (for multiphoton excitation it will be generally a matter of one stroke since only in this way should a sufficiently high local intensity be expected) is still not high enough to achieve a sufficient signal, the illumination stroke can be reduced in its width. The deficit of the reduced field can be (at least partially) balanced, if the stroke can be shifted perpendicular to the scan direction during the scan process, i.e. if the scan device 50 is designed to be bidirectional. The single axis-scanner 54 for thus reason must be replaced by a double axis-scan device (not shown). Since multiphoton microscopy is used very often for observation of neural structures which have one preferred direction, the "aisle scan" in many cases can detect all important picture elements although it extends over only a fraction of the visual field. One example of this aisle scan is shown in FIG. 6B as a modification of the example shown in FIG. 6A.

While in two-dimensional illumination patterns there are optimum angles into which the pattern must be linearly shifted in order to be able to achieve an optimum result from a minimum number of phase pictures, when using a strip pattern (i.e. one illumination pattern which is modulated only in one direction) there is fundamentally no preferred direction of displacement of the illumination pattern between the individual phase pictures as long as the displacement of one component in the direction transversely to the strips has one modulation phase and the at least required number of three different phase pictures can be taken. In order to be able to switch with the same measurement arrangement quickly and easily between a high-speed mode (with sequential strip structure and only three required phase pictures) and one high-resolution mode with for example a hexagonal illumination pattern with at least 7 phase pictures without more than the microlens array 14 upstream of the intermediate picture plane 30 (or the perforated mask or the phase plate, neither shown, in the intermediate picture plane 30) having to be replaced, the orientation of the beam deflection 16 is preferably chosen such that it allows the displacement angle which is optimum for the hexagonal pattern. Twice the displacement of a linear strip illumination for producing the (at least) three phase pictures can then be implemented using the same arrangement.

In addition to the described resolution increase in the illumination plane, the structured illumination also allows an increase in resolution in the z-direction. It results from the fact that for superficial illumination with a periodic pattern of coherent light, due to the Talbot effect a series of secondary foci automatically arise above and below the actual focal plane of the objective, the first secondary foci in both directions representing an inverted pattern with lower intensity. At the same time, all these foci in the z-direction are sharper than an individual, diffraction-limited focus. For the case of a 1-dimensional ruled grating, this has already been described by Gustafsson et al. Here a two-dimensional illumination with hexagonal structure also yields better results in the evaluated picture. The effect which is favorable for the resolution also arises when at the same time only three or more lines of a hexagonal pattern are illuminated.

Thus, with the method as claimed in the invention the resolution of an optical microscope both in the lateral and also in the axial direction can be clearly increased; this enables highly resolved three-dimensional pictures of the sample to be taken.

A mathematical derivation of the optimum displacement angle for a checkered pattern and for a hexagonal pattern is described below.

1. One-Dimensional Structured Illumination

In all methods which are common today for structured illumination, patterns with one or more frequencies in one direction of space are used. In doing so several phase pictures are taken between which the pattern or the picture of the pattern must be shifted. Assuming one frequency in one direction of space the intensity on one pixel (x, y) for the l-th phase picture can be written as $$I_l(x, y) = I_0 + I_s \cos(\underbrace{k_g}_{\frac{2\pi}{p_g}}(x - x_0) - \alpha_l)$$

$k_g$ being the space frequency of the grating, $p_g$ accordingly being the period and $x_0$ being the absolute location of the intensity peak relative to the zero point of the coordinate system. $I_0$ designates the non-confocal signal, $\alpha_l$ the amount of phase displacement and $I_s$ the so-called sectioning signal which for all pixels together yields an optical sectional view (or also quasi-confocal picture).

O.B.d.A. in the aforementioned equation the grating frequency is in the x direction.

The unknown variables in the aforementioned equation are $I_0$, $I_s$ and $x_0$ or $k_g x_0 =: \Phi_0$.

If the cos-function is written with complex exponential functions and uses $\Phi(x) := k_g x - \Phi_0$, we obtain $$I_l(x,y) = I_0 + \tfrac{1}{2} I_s e^{i\Phi(x)} e^{-i\alpha_l} + \tfrac{1}{2} I_s e^{-i\Phi(x)} e^{i\alpha_l} \quad (1)$$

For several values of the index l (which correspond to several phase pictures) (1) yields a system of linear equations. Based on the three unknowns $I_0$, $I_s$ and $\Phi$ at least 3 equations are needed to obtain a defined or even overdefined system of equations.

The solvability depends however also on which values for $\alpha_l$ are chosen.

Especially for 3 lines (therefore 3 phase pictures) this yields $$\begin{pmatrix} I_1 \\ I_2 \\ I_3 \end{pmatrix} = \underbrace{\begin{pmatrix} 1 & e^{-i\alpha_1} & e^{i\alpha_1} \\ 1 & e^{-i\alpha_2} & e^{i\alpha_2} \\ 1 & e^{-i\alpha_3} & e^{i\alpha_3} \end{pmatrix}}_{=:\hat{A}} \begin{pmatrix} I_0 \\ \tfrac{1}{2} I_s e^{i\Phi} \\ \tfrac{1}{2} I_s e^{-i\Phi} \end{pmatrix} \quad (2)$$

This 3×3 system of equations is solvable as long as the determinant of $\hat{A}$ not equal to 0, since exactly then $\hat{A}$ can be inverted. A system of equations which has been conditioned as well as possible is obtained by the choice of $$\alpha_l = \left\{ 0, \frac{2\pi}{3}, \frac{4\pi}{3} \right\},$$

for which the lines of $\hat{A}$ are orthogonal (maximum determinant).

$$\hat{A} = \begin{pmatrix} 1 & 1 & 1 \\ 1 & e^{-i\frac{2\pi}{3}} & e^{i\frac{2\pi}{3}} \\ 1 & e^{-i\frac{4\pi}{3}} & e^{i\frac{4\pi}{3}} \end{pmatrix}$$

$\hat{A}$ unitary in the case except for a factor $\sqrt{3}$, i.e. the inverse of $\hat{A}$ proportional to its adjoint matrix:

$$\hat{A}^{-1} = \frac{1}{3} \begin{pmatrix} 1 & 1 & 1 \\ 1 & e^{i\frac{2\pi}{3}} & e^{-i\frac{2\pi}{3}} \\ 1 & e^{i\frac{4\pi}{3}} & e^{-i\frac{4\pi}{3}} \end{pmatrix}$$

As a solution the sectional view is obtained $$I_s = \left| I_1 + I_2 e^{i\frac{2\pi}{3}} + I_3 e^{i\frac{4\pi}{3}} \right| = \sqrt{(I_1 - I_2)^2 + (I_2 - I_3)^2 + (I_3 - I_1)^2} \quad (3)$$

separately from the out-of-focus signal $$I_0 = I_1 + I_2 + I_3 \quad (4)$$

Equation (3) is known in the technical literature as a Wilson algorithm. (see for example http://www.aurox.co.uk/wp-content/uploads/som_1997_3.pdf) Another possibility for interpreting the aforementioned situation is to superimpose the (space frequency) spectrum of an individual phase picture:

In the focal plane of the microscope objective for linear fluorescence excitation the intensity distribution of the emission E(x, y) is given by $$E(\vec{x}) \propto O(\vec{x}) S(\vec{x})$$

$O(\vec{x})$ being the local density of fluorophores in the object and $S(\vec{x})$ being the intensity of the excitation light. Based on the convolution theorem for the spectrum of emission there results $$\tilde{E}(\vec{k}) \propto \tilde{O}(\vec{k}) * \tilde{S}(\vec{k}) = \int dk' \tilde{O}(\vec{k}\,') \tilde{S}(\vec{k} - \vec{k}\,'') \quad (5)$$

For the case that $S(\vec{x}) \equiv$ constant, $\tilde{S}(\vec{k}) \propto \delta(\vec{k})$ applies, therefore also $$\tilde{E}(\vec{k}) \propto \tilde{O}(\vec{k}).$$

When using a periodic excitation with a grating $$S(\vec{x}) = 1 + \cos(\vec{k}_g \vec{x} - \Phi_0)$$

a set of Dirac delta distributions for $\tilde{S}(\vec{k})$ arises:

$$\tilde{E}(\vec{k}) \propto \tilde{O}(\vec{k}) * \underbrace{\left( \delta(\vec{k}) + \frac{C_g}{2} \delta(\vec{k} - \vec{k}_g) e^{-i\Phi_0} + \frac{C_g}{2} \delta(\vec{k} + \vec{k}_g) e^{i\Phi_0} \right)}_{\tilde{S}(\vec{k})} = \quad (6)$$

$$= \tilde{O}(\vec{k}) + \frac{C_g}{2} \tilde{O}(\vec{k} - \vec{k}_g) e^{-i\Phi_0} + \frac{C_g}{2} \tilde{O}(\vec{k} + \vec{k}_g) e^{i\Phi_0} \quad (7)$$

$C_g$ designates the contrast of the grating which can be achieved for the case of an object with thickness 0 (therefore completely without the out-of-focus signal). With equation (7) it is apparent that the spectrum of the phase picture is composed of several superpositions of the object spectrum, and the origin has been shifted to the corresponding frequency each time.

After separation of these superimposed orders it is possible to compute a picture with increased lateral resolution (first of all in one direction).

(see for example http://www.msg.ucsf.edu/gustafsson/Files/JMicrosc198_82-87.pdf)

The separation of orders here functions exactly like the separation of the sectional view and the background. This concept is called superresolution below.

2. The Magic Angle 2.1 The Matrix $\hat{A}$

For the one-dimensional structure illumination the matrix $\hat{A}$ can have more than 3×3 entries. If the grating frequency is set to roughly n Airy, (analogously to equation (1)) n orders of diffraction in the picture of the grating are recombined:

$$I_l(\vec{x}) = I_0(\vec{x}) + \frac{1}{2}\sum_{m=1}^{n} I_s^{(m)}(\vec{x})e^{i\Phi_m(\vec{x})}e^{-i\alpha_{l,m}} + \quad (8)$$

$$\frac{1}{2}\sum_{m=1}^{n} \underbrace{I_s^{(-m)}(\vec{x})}_{I_s^{(m)}}\underbrace{e^{-i\Phi_m(\vec{x})}}_{e^{i\Phi_{-m}(\vec{x})}}\underbrace{e^{i\alpha_{l,m}}}_{e^{-i\alpha_{l,-m}}} =$$

$$= \underbrace{\frac{e^{i\cdot 0}}{e^{i\Phi_0(\vec{x})}}\underbrace{\frac{e^{-i\cdot 0}}{e^{-i\alpha_{l,0}}}}I_0(\vec{x}) + \sum_{m=1}^{n} e^{-i\alpha_{l,m}} \cdot \frac{1}{2}I_s^{(m)}(\vec{x})e^{i\Phi_m(\vec{x})} + \quad (9)$$

$$\sum_{m=-1}^{-n} e^{-i\alpha_{l,m}} \cdot \frac{1}{2}I_s^{(m)}(\vec{x})e^{i\Phi_m(\vec{x})}$$

The signal on the pixel $\vec{x}=(x, y)$ is therefore given by a superposition of N=2n+1 orders. The index l stands for the l-th phase picture, the index m designates the harmonic order of the respective frequency. $\Phi_m(\vec{x})=\vec{K}_m \circ \vec{x}$ applies.

Equation (9) can be written in matrix notation:

$$\begin{pmatrix} I_1(\vec{x}) \\ I_2(\vec{x}) \\ \vdots \\ I_M(\vec{x}) \end{pmatrix} = \hat{A} \cdot \begin{pmatrix} I_0(\vec{x}) \\ \frac{1}{2}I_s^{(1)}(\vec{x})e^{-i\Phi_1(\vec{x})} \\ \frac{1}{2}I_s^{(-1)}(\vec{x})e^{+i\Phi_1(\vec{x})} \\ \frac{1}{2}I_s^{(2)}(\vec{x})e^{+i\Phi_2(\vec{x})} \\ \vdots \\ \frac{1}{2}I_s^{(-n)}(\vec{x})e^{+i\Phi_n(\vec{x})} \end{pmatrix} \quad (10)$$

Measured Values

M designates the number of measurements taken (phase pictures). The vector on the right side of (10) has N=2n+1 entries, $\hat{A}$ therefore a M×N matrix.

So that $\hat{A}$ bijective and can be inverted, the following must apply

M=N and rang($\hat{A}$)=N.

The entries of $\hat{A}$ are given by $$\hat{A}_{l,m} = e^{-i\alpha_{l,m}} \quad (11)$$

If it is assumed that from one phase picture to the next the same lateral displacement $\vec{\Delta}$ always takes place and that the first phase picture (l=1) is not displaced at all, the following applies $$\alpha_{l,m} = (l-1)\delta\Phi_m = (l-1)\vec{k}_m \circ \vec{\Delta} \quad (12)$$

For the special case of a grating (o.B.d.A in x direction), $$\vec{k}_m = m\frac{2\pi}{p}\hat{e}_x \text{ and } \alpha_{l,m} = (l-1) \cdot m \cdot \Delta \frac{2\pi}{p} \cdot \cos(\theta)$$

θ designating the angle between the displacement direction and the x-axis and $\Delta = |\vec{\Delta}|$.

For the grating therefore any displacement direction except for the vertical to the frequency direction is possible.

If $$\Delta = \frac{p}{N}\frac{1}{\cos(\theta)}$$

is chosen, then $$\alpha_{l,m} = (l-1) \cdot m \cdot \frac{2\pi}{N} \quad (13)$$

$$\hat{A}_{l,m} = e^{-i(l-1)m\frac{2\pi}{N}}$$

for this special choice gives a discrete Fourier transform and the following applies $$\sum_m \hat{A}_{l,m}\hat{A}_{n,m}^* = \sum_{m=1}^{N} e^{-i(l-n)\cdot m\frac{2\pi}{N}} = N \cdot \delta_{l,n}$$

$\hat{A}$ therefore proportional to a unitary matrix.

Figure 7:
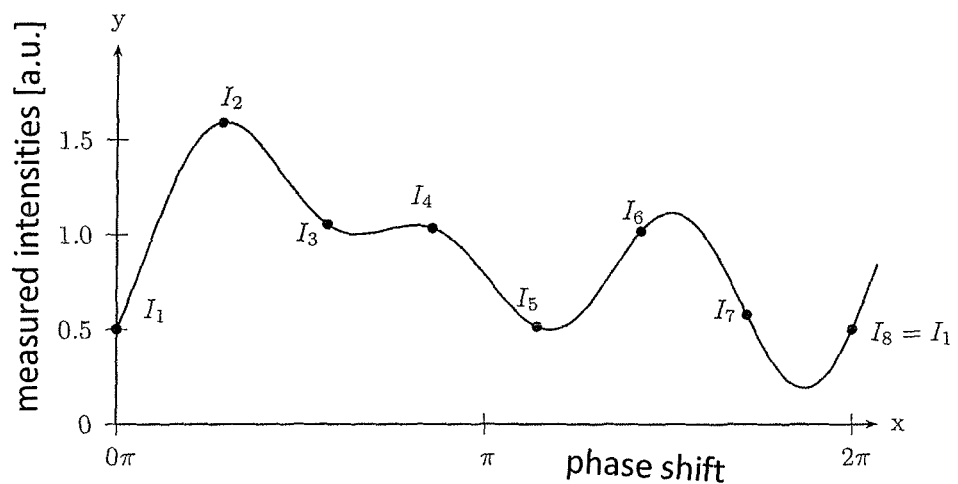
FIG. 7 show a sample characteristic of the signal on one detector pixel with continuous shifting of a hexagonal illumination pattern over the sample (solid line) or the measurement point which has been recorded for each phase picture (point $I_n$)

Clearly the signal on one pixel can be imagined as a periodic function (with N harmonic portions) which is scanned discretely with N points (see FIG. 7)).

Figure 8:
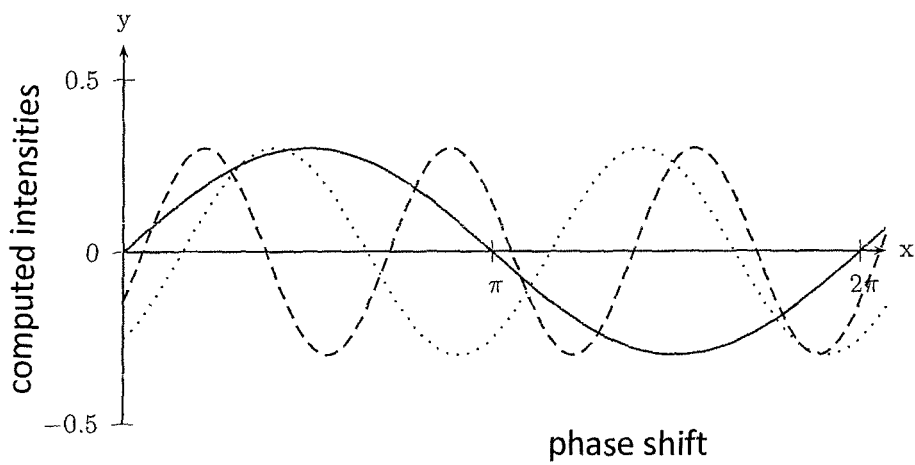
FIG. 8 shows the individual harmonic portions from FIG. 7 for the first (solid), the second (broken) and the third (dotted) order.

Since the relative strengths of the harmonic portions are sought, the discrete Fourier transform is the correct transform. FIG. 8) shows the mathematically decomposed portions from FIG. 7).

The representation in equation (10) then also applies when instead of a grating a more general periodic structure (with orders of frequencies in several directions) is used. In order to attain an optimally solvable situation for more general periodic structures, as described here, the $\alpha_{l,m}$ (therefore the phase displacement for the l-th order in the m-th phase picture) should be able to be written as in equation (13):

$$\alpha_{l,m} = (m-1) \cdot l \cdot \frac{2\pi}{N}$$

and the Fourier orders for structures with frequencies in several directions can be indicated as wished.

Optimally solvable in this connection means an optimum conditioning of the matrix or a minimum condition number. The condition number of a matrix indicates how errors propagate in the solution of a system of linear equations. The smallest possible value for the condition number would therefore be 1:

$$\hat{A}\vec{x} = \vec{y} \quad (14)$$

$$\Rightarrow \vec{x} = \hat{A}^{-1}\vec{y} \quad (15)$$

$$\Rightarrow \frac{\|\delta\vec{x}\|}{\|x\|} \le \frac{\|\delta\vec{y}\|}{\|y\|} \cdot cond(\hat{A}) \quad (16)$$

$$cond(\hat{A}) := \|\hat{A}\| \cdot \|\hat{A}^{-1}\| \quad (17)$$

The condition number is minimal (1) for the case in which $\hat{A}$ a unitary matrix. (The eigen values of a unitary matrix (and their inverses) are all on the unit circle in $\mathbb{C}$, from which with (17) it follows that cond($\hat{A}$)=1·1=1).

2.2 Chessboard

As an expansion of the aforementioned method it was considered whether frequency portions in several directions can also be separated from one another by using a structure which contains frequencies in several directions when this structure is displaced only in one direction when the phase pictures are being produced.

On the one hand, the motivation for this is that the conventional method for quasi-confocal structure illumination (grating in one orientation, no rotation) is very anisotropic, i.e. that contrasts are reconstructed from the focal plane only in one direction.

On the other hand, the evaluation of frequency portions in more than one direction makes a superresolution evaluation possible without rotating the structure relative to the optical axis and with few phase pictures. That the displacement takes place only in one direction simplifies the use of structured illumination with superresolution and makes the concept faster and more robust.

If the situation is compared to that in equation (2), it is apparent that the mathematical problem consists in marking the individual frequencies with one explicit phase displacement at a time and in thus making them distinguishable.

The Fourier representation of a chessboard $\mathfrak{S}(x, y)$ with edge length a is $$\mathfrak{S}(x, y) \propto \quad (18)$$

$$\int d\vec{k} e^{i\vec{k}(\vec{x}-\vec{x}_0)} \left( \sum_{m,n=-\infty}^{+\infty} \delta\left(\vec{k} - \frac{\pi}{a}\binom{m}{n}\right) \right) \quad (19)$$

$$\operatorname{sinc}\left(\frac{k_x a}{2}\right)\operatorname{sinc}\left(\frac{k_y a}{2}\right) \cdot \cos\left[\frac{a}{2}(k_x + k_y)\right] = \quad (20)$$

$$\sum_{m,n=-\infty}^{+\infty} e^{i\frac{\pi}{a}(\vec{x}-\vec{x}_0)\binom{m}{n}} \operatorname{sinc}\left(\frac{\pi m}{2}\right)\operatorname{sinc}\left(\frac{\pi n}{2}\right)\cos\left[\frac{\pi}{2}(m+n)\right] = \quad (21)$$

$$\sum_{m,n=-\infty}^{+\infty} e^{i\frac{\pi}{a}((x-x_0)m+(y-y_0)n)} \operatorname{sinc}\left(\frac{\pi m}{2}\right)\operatorname{sinc}\left(\frac{\pi n}{2}\right)\cos\left[\frac{\pi}{2}(m+n)\right] = \quad (22)$$

$$1 + \sum_{m,n} \left(\frac{2(-1)^{\frac{m-1}{2}}}{m\pi}\right)\left(\frac{2(-1)^{\frac{n-1}{2}}}{n\pi}\right) e^{i\frac{\pi}{a}[(x-x_0)m+(y-y_0)n]} \quad (23)$$

(m+n) straight

Figure 9:
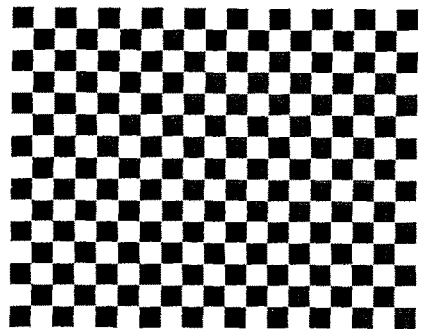
FIG. 9 shows a checkered pattern according to equation (23)

The chessboard is oriented in this representation as is also conventional in chess games or as is shown in FIG. 9).

The space frequency vectors of the chessboard are therefore generally given by $$\vec{k}_{m,n} = \frac{\pi}{a}\binom{m}{n}$$

If the frequency of the chessboard is chosen to be near the resolution boundary of the microscope objective lens, only the first orders are $\vec{k}_{1,1} =: \vec{k}^+$ und $\vec{k}_{1,-1} =: \vec{k}^-$ are recombined into a picture:

$$\mathfrak{S}(x, y) \propto 1 + \frac{8}{\pi^2}\cos\left[\frac{\pi}{a}(x+y) - \Phi_0^+\right] + \frac{8}{\pi^2}\cos\left[\frac{\pi}{a}(x-y) - \Phi_0^-\right]$$

The two frequency directions of the chessboard are indexed here with + and −.

Analogously to equation (1) the following is obtained $$I(x, y) = I_0 + I_s^+ \frac{8}{\pi^2}\cos\left[\frac{\pi}{a}(x+y) - \Phi_0^+\right] + I_s^- \frac{8}{\pi^2}\cos\left[\frac{\pi}{a}(x-y) - \Phi_0^-\right] \quad (24)$$

Compared to (1) there are 5 unknowns here $I_0$, $I_s^{\pm}$ and $\Phi_0^{\pm}$. Therefore at least 5 phase pictures are necessary to determine the unknowns. (N=5).

The phase displacement which arises for a lateral displacement by $\vec{\Delta} = (\Delta_x, \Delta_y)$ for order i is $$\delta\Phi_i = \vec{k}_i \circ \vec{\Delta}$$

therefore given by the orthogonal projection of the displacement vector onto the frequency vector $\vec{k}_i$.

In order to obtain a unitary matrix as in equation (2) for $\hat{A}$, therefore a displacement vector $\vec{\Delta}$ is sought so that $$\boxed{\begin{array}{l}\vec{k}^+ \circ \vec{\Delta} = \delta\Phi_+ \\ \vec{k}^- \circ \vec{\Delta} = \delta\Phi_- = \kappa\delta\Phi_+\end{array}}$$

$$\Leftrightarrow$$

$$\boxed{\begin{array}{l}\Delta_x + \Delta_y = \frac{a}{\pi}\delta\Phi_+ \\ \Delta_x - \Delta_y = \kappa\frac{a}{\pi}\delta\Phi_+\end{array}}$$

$$\Leftrightarrow$$

$$\boxed{\begin{array}{l}\Delta_x = \frac{(1+\kappa)a}{2\pi}\delta\Phi_+ \\ \Delta_y = \frac{(1-\kappa)a}{2\pi}\Phi_{shift}\end{array}}$$

With one parameter κ still to be determined.

For any value of κ the aforementioned equations can be satisfied if the displacement vector Δ includes an angle θ to the x-axis so that $$\boxed{\tan(\theta) = \frac{\Delta_y}{\Delta_x} \Rightarrow \theta - \arctan\left(\frac{1-\kappa}{1+\kappa}\right)}$$

The phase displacements $\alpha_{l,m}$ are given here by $$\alpha_{l,0} \equiv 0 \tag{25}$$

$$\alpha_{l,+} = (l-1)\Delta \frac{2\pi}{a}\cos(\gamma) \tag{26}$$

$$\alpha_{l,-} = (l-1)\kappa\Delta \frac{2\pi}{a}\cos(\gamma) \tag{27}$$

$\gamma$ designating the angle between $\vec{\Delta}$ and $\vec{k}^+$ ($\theta = \gamma + 45°$). If for path of the displacement $\Delta =$ $$\Delta = \frac{a}{5\cos(\gamma)}$$

is chosen, there arises $$\alpha_{l,+} = (l-1)\frac{2\pi}{5} \tag{28}$$

$$\alpha_{l,-} = (l-1)\kappa\frac{2\pi}{5} \tag{29}$$

It can be shown that there are two possible values for $\kappa$, so that $\hat{A} = \exp(-i\alpha_{l,m})$ is a unitary matrix:

$$\kappa_1 = 2 \tag{30}$$

$$\kappa_2 = 3 \tag{31}$$

This means that one solution is possible under 2 different orientation angles.

Viewed technically, the solution should be preferred in which the smaller angle for $\gamma = \theta - 45°$ arises. This is due on the one hand to the absolute displacement $$\Delta = \frac{a}{5}\frac{1}{\cos(\gamma)}$$

becoming larger with increasing $\gamma$. But it should not be unconditionally larger than necessary. On the other hand the error of $\kappa$ is directly dependent on $\alpha_{l,-}$. For the error of $\kappa$ there arises $$\delta\kappa = \delta\left(\frac{\cos(90° - \gamma)}{\cos\gamma}\right) = \delta(\tan(\gamma)) = (1 + \tan^2(\gamma))\delta\gamma \tag{32}$$

One possible orientation error of the chessboard therefore has greater effects on the conditioning of the matrix $\hat{A}$ at a larger value of $\gamma$.

Based on these considerations, more preferably $\theta_1$ should be used for the chessboard as the magic angle.

$$\theta_1 = \arctan(-\frac{1}{3}) \approx -18.435°$$

The second possible angle would be $\theta_2 = \arctan(-\frac{1}{2}) \approx -26.565°$.

By interchanging the frequencies labeled + and − above, it is apparent that an angle of +18.435° is possible.

If the displacement direction o.B.d.A is placed along the x-axis, the aforementioned condition is attained by turning the chessboard pattern.

After rotation by +18.435° the chessboard is given by:

$$1 + \underbrace{\frac{8}{\pi^2}\cos(\frac{2\pi}{\sqrt{10}\,a}(2x+y) - \Phi_0^+)}_{\Phi^+(\vec{x})} + \underbrace{\frac{8}{\pi^2}\cos(\frac{2\pi}{\sqrt{10}\,a}(x+2y) - \Phi_0^-)}_{\Phi^-(\vec{x})}$$

By interchanging x and y the representation for the case of a rotation of the pattern by −18.435° is obtained.

The l-th phase picture of the chessboard on the camera is $$I_l(x,y) = I_0 + I_s^+ \frac{8}{\pi^2}\cos(\Phi^+(\vec{x}) - 2\alpha_l) + I_s^- \frac{8}{\pi^2}\cos(\Phi^{-1}(\vec{x}) - \alpha_l)$$

According to the $\alpha_{l,m}$ from equations (28)-(31) with $\kappa_1 = 2$ for $\hat{A}$ there is:

$$\hat{A} = \frac{1}{\sqrt{5}}\begin{pmatrix} 1 & 1 & 1 & 1 & 1 \\ 1 & \exp\left(-i\frac{2\pi}{5}\right) & \exp\left(-i\frac{8\pi}{5}\right) & \exp\left(-i\frac{4\pi}{5}\right) & \exp\left(-i\frac{6\pi}{5}\right) \\ 1 & \exp\left(-i\frac{4\pi}{5}\right) & \exp\left(-i\frac{6\pi}{5}\right) & \exp\left(-i\frac{8\pi}{5}\right) & \exp\left(-i\frac{2\pi}{5}\right) \\ 1 & \exp\left(-i\frac{6\pi}{5}\right) & \exp\left(-i\frac{4\pi}{5}\right) & \exp\left(-i\frac{2\pi}{5}\right) & \exp\left(-i\frac{8\pi}{5}\right) \\ 1 & \exp\left(-i\frac{8\pi}{5}\right) & \exp\left(-i\frac{2\pi}{5}\right) & \exp\left(-i\frac{6\pi}{5}\right) & \exp\left(-i\frac{4\pi}{5}\right) \end{pmatrix}$$

This matrix is unitary, thus the inverse is exactly $$\hat{A}^{-1} = \frac{1}{\sqrt{5}}\begin{pmatrix} 1 & 1 & 1 & 1 & 1 \\ 1 & \exp\left(i\frac{2\pi}{5}\right) & \exp\left(i\frac{4\pi}{5}\right) & \exp\left(i\frac{6\pi}{5}\right) & \exp\left(i\frac{8\pi}{5}\right) \\ 1 & \exp\left(i\frac{8\pi}{5}\right) & \exp\left(i\frac{6\pi}{5}\right) & \exp\left(i\frac{4\pi}{5}\right) & \exp\left(i\frac{2\pi}{5}\right) \\ 1 & \exp\left(i\frac{4\pi}{5}\right) & \exp\left(i\frac{8\pi}{5}\right) & \exp\left(i\frac{2\pi}{5}\right) & \exp\left(i\frac{6\pi}{5}\right) \\ 1 & \exp\left(i\frac{6\pi}{5}\right) & \exp\left(i\frac{2\pi}{5}\right) & \exp\left(i\frac{8\pi}{5}\right) & \exp\left(i\frac{4\pi}{5}\right) \end{pmatrix}$$

For the solutions of the sectional views therefore there arise $$I_0 = I_1 + I_2 + I_3 + I_4 + I_5 \tag{33}$$

$$I_s^+ = \left| I_1 + I_2 e^{i\frac{2\pi}{5}} + I_3 e^{i\frac{4\pi}{5}} + I_4 e^{i\frac{6\pi}{5}} + I_5 e^{i\frac{8\pi}{5}} \right| \tag{34}$$

$$I_s^- = \left| I_1 + I_2 e^{i\frac{4\pi}{5}} + I_3 e^{i\frac{8\pi}{5}} + I_4 e^{i\frac{2\pi}{5}} + I_5 e^{i\frac{6\pi}{5}} \right| \tag{35}$$

The other two solutions are complexly conjugated to the cited solutions for $I_s^+$ and $I_s^-$. For the root mean square from $I_s^+$ and $I_s^-$, therefore $\sqrt{\langle I_s^2 \rangle} = \sqrt{(I_s^+)^2 + (I_s^-)^2}$, there arises $$\sqrt{\langle I_s^2 \rangle} = \sqrt{(I_1 - I_3)^2 + (I_2 - I_4)^2 + (I_3 - I_5)^2 + (I_4 - I_1)^2 + (I_5 - I_2)^2} \tag{36}$$

In practice the orientation angle of the pattern $\theta$ will have an error. This error can be measured and compensated in the aforementioned evaluation.

In a calibration recording, a number of phase pictures are recorded on a layer which is fluorescing as uniformly as possible (so that $\tilde{O}(\vec{k}) \approx \iota(\vec{k})$) in which the pattern is displaced from one picture to the next by the same unknown phase each time. If the frequency of the chessboard in the sample is known, this phase displacement can be set roughly to a theoretical value of one tenth period. (It is only important to choose the displacement not to be too large during calibration).

Analogously to equation (7), in this situation for the space frequency spectrum of the picture there arises the following:

$$E_l(\vec{k}) \propto \underbrace{\delta(\vec{k})}_{\approx \tilde{O}(\vec{k})} + \frac{C_s^+}{2}\delta(\vec{k}-\vec{k}^+)e^{-i(\Phi_0^+ + l\alpha^+)} +$$

$$\frac{C_s^+}{2}\delta(\vec{k}-\vec{k}^+)e^{i(\Phi_0^+ + l\alpha^+)} + + \frac{C_s^-}{2}\delta(\vec{k}+\vec{k}^-)e^{-i(\Phi_0^- + l\alpha^-)} +$$

$$\frac{C_s^-}{2}\delta(\vec{k}+\vec{k}^-)e^{i(\Phi_0^- + l\alpha^-)}$$

In the Fourier transforms of this series of calibration phase pictures then the respectively positive peaks (therefore the ones with $\iota(\vec{K}-\vec{K}^{\pm})$) of the chessboard orders are then sought and their real parts are evaluated as a function of the picture index.

$$\Re\left(\frac{C_s^{\pm}}{2}\delta(\vec{k}-\vec{k}^{\pm})e^{-i(\Phi_0^{\pm}+l\alpha^{\pm})}\right) = \frac{C_s^{\pm}}{2}\delta(\vec{k}-\vec{k}^{\pm})\cos(\Phi_0^{\pm}+l\alpha^{\pm})$$

A fit to the model $$a+b\cos(cx+d) \quad (37)$$

thus yields the contrast on the calibration object $$C_s^{\pm} = 2\frac{b}{a},$$

the start phase $\Phi_0^{\pm}=d$ and the sought phase displacement $\alpha_l^{\pm}=c^{\pm}$ for each frequency direction of the chessboard. The determined phase displacements for the + and − direction yield the orientation angle of the pattern relative to the displacement direction $$\theta = \arctan\left(\frac{c^+ - c^-}{c^+ + c^-}\right) \quad (38)$$

The ratio of $c^+$ and $c^-$ is identical to the above defined parameter $\kappa$ and can be considered in the matrix $\hat{A}$:

$$\frac{c^+}{c^-} = \kappa \quad (39)$$

$$\hat{A} = \frac{1}{\sqrt{5}}\begin{pmatrix} 1 & 1 & 1 & 1 & 1 \\ 1 & \exp\left(-i\frac{2\pi}{5}\right) & \exp\left(-i\frac{8\pi}{5}\right) & \exp\left(-i\kappa\frac{2\pi}{5}\right) & \exp\left(-i\kappa\frac{8\pi}{5}\right) \\ 1 & \exp\left(-i\frac{4\pi}{5}\right) & \exp\left(-i\frac{6\pi}{5}\right) & \exp\left(-i\kappa\frac{4\pi}{5}\right) & \exp\left(-i\kappa\frac{6\pi}{5}\right) \\ 1 & \exp\left(-i\frac{6\pi}{5}\right) & \exp\left(-i\frac{4\pi}{5}\right) & \exp\left(-i\kappa\frac{6\pi}{5}\right) & \exp\left(-i\kappa\frac{4\pi}{5}\right) \\ 1 & \exp\left(-i\frac{8\pi}{5}\right) & \exp\left(-i\frac{2\pi}{5}\right) & \exp\left(-i\kappa\frac{8\pi}{5}\right) & \exp\left(-i\kappa\frac{2\pi}{5}\right) \end{pmatrix} \quad (40)$$

For the magic angle $\kappa=2$ and $\hat{A}$ unitary. For deviations a corrected evaluation is obtained when $\hat{A}$ inverted.

The aforementioned solution can be carried out analogously for the 2 possible magic angles $\theta_2$.

2.3 Hexagon

Alternatively to the above described chessboard pattern it is also possible with a hexagonal pattern to evaluate the phase pictures which were recorded as the pattern is displaced in one direction of space.

The motivation for this is that the hexagon contains frequencies in 3 directions of space. In the prior art for superresolution structured illumination a grating is used for which phase pictures are recorded in 3 orientations of the grating. Conventionally an angle of 120° for the orientations of the grating are chosen in order to finally obtain a relatively isotropic point spread function. Exactly this angle also exists between the base frequency directions of the hexagon.

Figure 10:
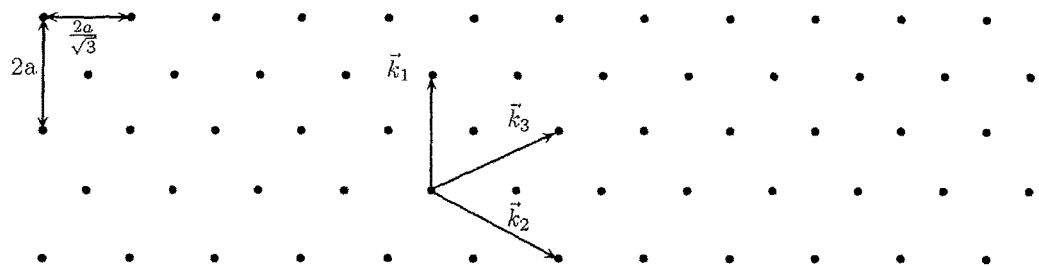
FIG. 10 shows a hexagonal pattern according to equation (41)

For a hexagonal pattern $\mathfrak{H}(\vec{x})$ with base period a, as shown in FIG. 10), $$\mathfrak{H}(\vec{x}) = \sum_{m,n} \delta\left(x - m\frac{2a}{\sqrt{3}}\right)\delta(y-n2a) + \quad (41)$$

$$\sum_{m,n} \delta\left(x - \left(m+\frac{1}{2}\right)\frac{2a}{\sqrt{3}}\right)\delta\left(y - \left(n+\frac{1}{2}\right)2a\right)$$

the Fourier representation reads $$\mathfrak{H}(\vec{x}) = \sum_{m,n}(1+e^{-i(m\pi+n\pi)})e^{i\left(m\sqrt{3}\frac{\pi}{a}x+n\frac{\pi}{a}y\right)} = 2\sum_{m,n} e^{i\left(m\sqrt{3}\frac{\pi}{a}x+n\frac{\pi}{a}y\right)} \quad (42)$$

$(m+n)$ straight

For the frequency vector in general the following arises:

$$\vec{k}_{m,n} = \frac{\pi}{a}\begin{pmatrix} m\sqrt{3} \\ n \end{pmatrix} \quad (43)$$

On a circle with the radius of the base frequency $$|\vec{k}| = \frac{2\pi}{a},$$

as expected there are 3 base frequency vectors $\vec{k}_{0,2}$, $\vec{k}_{1,1}$ and $\vec{k}_{1,-1}$ of the hexagon:

$$\vec{k}_{0,2} = \frac{2\pi}{a}\begin{pmatrix} 0 \\ 1 \end{pmatrix} =: \vec{k}_1 \quad (44)$$

$$\vec{k}_{1,-1} = \frac{\pi}{a}\begin{pmatrix} \sqrt{3} \\ -1 \end{pmatrix} =: \vec{k}_2 \quad (45)$$

$$\vec{k}_{1,1} = \frac{\pi}{a}\begin{pmatrix} \sqrt{3} \\ 1 \end{pmatrix} =: \vec{k}_3 \quad (46)$$

When interchanging the signs of m and n the pertinent negative frequency vectors are obtained.

Here an important property of the hexagonal symmetry is apparent, specifically that the frequency vectors of the base frequency span an equilateral triangle, or that the following applies:

$$\vec{k}_1 + \vec{k}_2 = \vec{k}_3 \tag{47}$$

If only the first orders are examined, the following is obtained $$\mathfrak{J} \propto 1 + \frac{1}{3}\cos\underbrace{\left(\frac{2\pi}{a}y - \Phi_0^1\right)}_{=:\Phi^1(\vec{x})} + \\ \frac{1}{3}\cos\underbrace{\left(\frac{\pi}{a}(\sqrt{3}x - y) - \Phi_0^2\right)}_{\Phi^2(\vec{x})} + \frac{1}{3}\cos\underbrace{\left(\frac{\pi}{a}(\sqrt{3}x - y) - \Phi_0^3\right)}_{\Phi^3(\vec{x})} \tag{48}$$

or the measured intensity of the phase pictures (corresponding to equation (24)) is obtained $$I_1(x,y) = I_0 + I_s^{(1)}\cos(\Phi^1(\vec{x}) - \alpha_l^1) + \\ I_s^{(2)}\cos(\Phi^2(\vec{x}) - \alpha_l^2) + I_s^{(3)}\cos(\Phi^3(\vec{x}) - \alpha_l^3) \tag{49}$$

For the case of the hexagon there are 7 unknown variables ($I_0$, $I_s^{(1),(2),(3)}$, $\Phi^{(1),(2),(3)}(\vec{x})$), therefore 7 phase pictures are needed for an evaluation. (N=7)

Analogously to the chessboard, for a hexagon the following can be written:

$$\vec{k}_1 \circ \vec{\Delta} = \delta\Phi_1$$

$$\vec{k}_2 \circ \vec{\Delta} = \delta\Phi_2 = \kappa\delta\Phi_1$$

then according to (47) the following also applies $$\vec{k}_3 \circ \vec{\Delta} = \delta\Phi_3 = (1+\kappa)\delta\Phi_1$$

$\Phi_{Shift}$ representing any phase displacement.

Insertion Yields $$\boxed{\begin{aligned} \vec{k}_1 \circ \vec{\Delta} &= \delta\Phi_1 \\ \vec{k}_2 \circ \vec{\Delta} &= \kappa\delta\Phi_1 \end{aligned}}$$

$$\Leftrightarrow$$

$$\boxed{\begin{aligned} \frac{2\pi}{a}\Delta_y &= \delta\Phi_1 \\ \frac{\pi}{a}\sqrt{3}\Delta_x - \frac{\pi}{a}\Delta_y &= \kappa\delta\Phi_1 \end{aligned}}$$

$$\Leftrightarrow$$

$$\boxed{\begin{aligned} \Delta_x &= \frac{a(2\kappa+1)}{2\pi\sqrt{3}}\delta\Phi_1 \\ \Delta_y &= \frac{a}{2\pi}\delta\Phi_1 \end{aligned}}$$

The aforementioned conditions can be achieved if for the angle between the displacement vector and the x axis an angle of $$\boxed{\tan(\theta) = \frac{\Delta_y}{\Delta_x} \Rightarrow \theta = \arctan\left(\frac{\sqrt{3}}{(2\kappa+1)}\right)}$$

is set.

For the phase displacements $\alpha_{l,m}$ the following are obtained here:

$$\alpha_{l,0} \equiv 0 \;\forall\; l \tag{50}$$

$$\alpha_{l,\pm 1} = \pm(l-1)\Delta\frac{2\pi}{a}\cos(\gamma) \tag{51}$$

$$\alpha_{l,\pm 2} = \pm(l-1)\kappa\Delta\frac{2\pi}{a}\cos(\gamma) \tag{52}$$

$$\alpha_{l,\pm 3} = \pm(l-1)(1+\kappa)\Delta\frac{2\pi}{a}\cos(\gamma) \tag{53}$$

$\gamma$ being the angle between $\vec{\Delta}$ and $\vec{k}_1$.

Again $$\Delta = \frac{a}{N\cos\gamma} = \frac{a}{7\cos\gamma}$$

is chosen and the following is obtained $$\alpha_{l,\pm 1} = \pm(l-1)\frac{2\pi}{7} \tag{54}$$

$$\alpha_{l,\pm 2} = \pm(l-1)\kappa\frac{2\pi}{7} \tag{55}$$

$$\alpha_{l,\pm 3} = \pm(l-1)(1+\kappa)\frac{2\pi}{7} \tag{56}$$

Exactly as in the chessboard method, it can also be shown here than 2 possible values for $\kappa$ lead to a unitary matrix $\hat{A}$:

$$\kappa_1 = 2 \tag{57}$$

$$\kappa_2 = 4 \tag{58}$$

Therefore again 2 orientation angles between the displacement vector and the x-axis are possible, from analogous consideration as in the chessboard that angle being chosen for which the smaller value for $\gamma=\theta-90°$ arises. ($\delta_\kappa = \frac{1}{2}\sqrt{3}(1+\tan^2(\gamma))$)

$$\boxed{\theta_1 = \arctan\left(\frac{\sqrt{3}}{5}\right) \approx 19.107°} \tag{59}$$

The second (theoretically) possible angle would be $$\theta_2 = \arctan\frac{\sqrt{3}}{9}$$
$$\approx 10.893°.$$

Based on the 60° symmetry of the hexagonal pattern and with consideration of the negative frequency directions it is apparent that all angles from $\{n60°\pm 19.107° | n\in\mathbb{Z}\}$ are possible.

The angle between x-axis and $\vec{\Delta}$ is $\theta_1 - 90° \approx -70.89°$ here.

If as above o.B.d.A. $\vec{\Delta}$ is chosen in the direction of the x-axis, the hexagonal pattern must be turned by 70.89° in order to bring it into the desired orientation.

According to $\alpha_{l,m}$ from (50)-(56), with $\kappa_1=2$ for $\hat{A}$ the following arises:

$$\hat{A} = \frac{1}{\sqrt{7}} \begin{pmatrix} 1 & 1 & 1 & 1 & 1 & 1 & 1 \\ 1 & e^{-i\frac{2\pi}{7}} & e^{-i\frac{12\pi}{7}} & e^{-i\frac{4\pi}{7}} & e^{-i\frac{10\pi}{7}} & e^{-i\frac{6\pi}{7}} & e^{-i\frac{8\pi}{7}} \\ 1 & e^{-i\frac{4\pi}{7}} & e^{-i\frac{10\pi}{7}} & e^{-i\frac{8\pi}{7}} & e^{-i\frac{6\pi}{7}} & e^{-i\frac{12\pi}{7}} & e^{-i\frac{2\pi}{7}} \\ 1 & e^{-i\frac{6\pi}{7}} & e^{-i\frac{8\pi}{7}} & e^{-i\frac{12\pi}{7}} & e^{-i\frac{2\pi}{7}} & e^{-i\frac{4\pi}{7}} & e^{-i\frac{10\pi}{7}} \\ 1 & e^{-i\frac{8\pi}{7}} & e^{-i\frac{6\pi}{7}} & e^{-i\frac{2\pi}{7}} & e^{-i\frac{12\pi}{7}} & e^{-i\frac{10\pi}{7}} & e^{-i\frac{4\pi}{7}} \\ 1 & e^{-i\frac{10\pi}{7}} & e^{-i\frac{4\pi}{7}} & e^{-i\frac{6\pi}{7}} & e^{-i\frac{8\pi}{7}} & e^{-i\frac{2\pi}{7}} & e^{-i\frac{12\pi}{7}} \\ 1 & e^{-i\frac{12\pi}{7}} & e^{-i\frac{2\pi}{7}} & e^{-i\frac{10\pi}{7}} & e^{-i\frac{4\pi}{7}} & e^{-i\frac{8\pi}{7}} & e^{-i\frac{6\pi}{7}} \end{pmatrix}$$

For the solutions specifically the following arises:

$$I_0 = I_1 + I_2 + I_3 + I_4 + I_5 + I_6 + I_7 \quad (60)$$

$$I_s^{(1)} = \left| I_1 + I_2 e^{i\frac{2\pi}{7}} + I_3 e^{i\frac{4\pi}{7}} + I_4 e^{i\frac{6\pi}{7}} + I_5 e^{i\frac{8\pi}{7}} + I_6 e^{i\frac{10\pi}{7}} + I_7 e^{i\frac{12\pi}{7}} \right| \quad (61)$$

$$I_s^{(2)} = \left| I_1 + I_2 e^{i\frac{4\pi}{7}} + I_3 e^{i\frac{8\pi}{7}} + I_4 e^{i\frac{12\pi}{7}} + I_5 e^{i\frac{2\pi}{7}} + I_6 e^{i\frac{6\pi}{7}} + I_7 e^{i\frac{10\pi}{7}} \right| \quad (62)$$

$$I_s^{(3)} = \left| I_1 + I_2 e^{i\frac{6\pi}{7}} + I_3 e^{i\frac{12\pi}{7}} + I_4 e^{i\frac{4\pi}{7}} + I_5 e^{i\frac{10\pi}{7}} + I_6 e^{i\frac{2\pi}{7}} + I_7 e^{i\frac{8\pi}{7}} \right| \quad (63)$$

$$<I_s^2> = \sqrt{\begin{array}{l}(I_1-I_4)^2 + (I_2-I_5)^2 + (I_3-I_6)^2 + (I_4-I_7)^2 + \\ +(I_5-I_1)^2 + (I_6-I_2)^2 + (I_7-I_3)^2\end{array}} \quad (64)$$

Exactly as in a chessboard, for the hexagon errors in the orientation can be determined by calibration and can likewise be compensated in the evaluation.

Based on the condition (47) for the hexagon there is one possibility for making a plausibility test:

For the calibration on all 3 orders the following must (roughly) always apply:

$$c_1 + c_2 = c_3$$

$c_k$ meaning the same fit parameters as in equation (37).

Thus for example for an automated system it is always possible to ascertain whether a certain calibration recording (or also evaluation) was defined analogously or erroneously.

Even if the grating contains only 1 order of diffraction as in Chapter 1, more than 3 phase pictures can be computed to one solution. If N phase pictures are taken, N frequency orders can be detached from one another. If only one order is contained, for the other orders as the solution 0 arise.

This means on the other hand that equations (33-35) can also be applied to the grating with a relative phase displacement of $$\frac{2\pi}{5}.$$

Here then 5 pictures must be taken. The nontrivial solutions are (33) and (34) here.

In exactly the same way equations (60) to (63) can be applied to a grating pattern and a chessboard-like pattern when exactly $$\frac{2\pi}{7}$$

is chosen as the relative phase displacement between the phase pictures and a total of 7 phase pictures are taken.

The parameter $\kappa$ and its error can be formulated independently of the pattern used:

$$\kappa = \cos(\theta_s) - \sin\theta_s \tan\gamma \quad (65)$$

$$\delta_\kappa = \sin\theta_2(1 + \tan^2\gamma)\delta\gamma \quad (66)$$

$\theta_s$ being the angle of symmetry of the structure $\theta_s = \{$

90° for a chessboard

60° for a hexagon and $\gamma$ as above being the angle between $\vec{k}_1$ and $\vec{\Delta}$.

2.3.1. Contrast for the Hexagon

In contrast to a grating pattern or chessboard pattern a hexagonal pattern has a fill factor of ⅓ (instead of ½).

Figure 11:
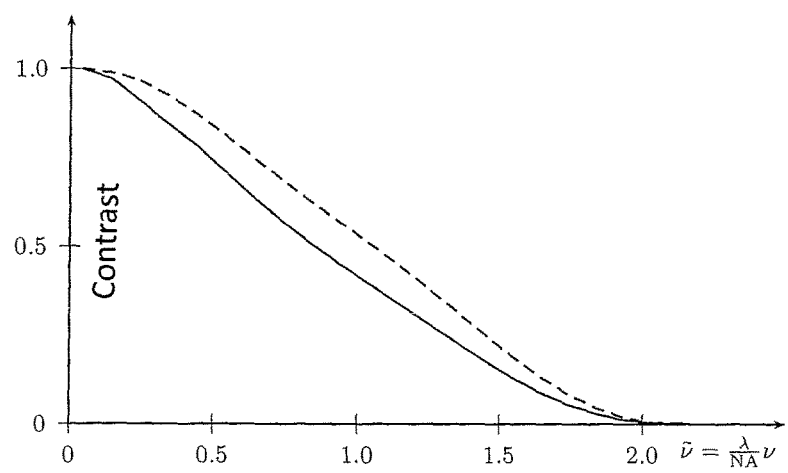
FIG. 11 shows contrast characteristics for a hexagonal pattern (broken line) and for a ruled grating (solid line) as a function of the normalized structure frequency.

This leads on the one hand to a reduced amount of light in the sample, on the other hand based on the fill factor for the hexagon a somewhat different modulation transfer function arises (shown in FIG. 11)).

$$\tilde{v} = \frac{\lambda}{NA}$$

is the structure frequency which is normalized (to the PSF half-value width) and which in each case must be between 0 and 2. ($\tilde{v}=2$ corresponds exactly to the optical cut-off frequency). For quasiconfocal structured illumination a structure frequency of $\tilde{v} \approx 1$ is especially favorable since the picture of the structure for this frequency in the z-direction has a minimum half-value width. For this frequency in the incoherent case a contrast which is roughly 1.28 times stronger arises for the hexagon.

In the coherent case the effect is must less dramatically pronounced, but in the coherent case phase substrates can also be used which in turn lead to clearly higher contrasts.

2.4 Geometrical Interpretation 2.4.1 Chessboard

Assuming equation (12), $$\alpha_{l,m} = (l-1)\vec{k}_m \circ \vec{\Delta} = (l-1)|\vec{k}_m||\Delta|\cos(\theta_m)$$

it is apparent that the entries of $\alpha_{l,m}$ (and thus also the entries of $\hat{A}$) are dependent on the orthogonal projection of the displacement vector $\vec{\Delta}$ onto the respective frequency vector.

Figure 12:
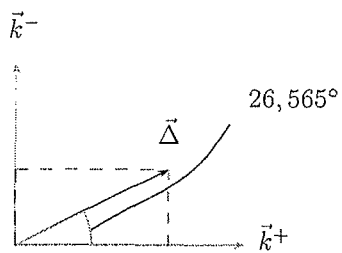
FIG. 12 shows the orthogonal projection of the displacement vector in the frequency space in the first order for a checkered illumination pattern.

For the magic angle in the chessboard the orthogonal projection of the displacement vector onto the frequency vector $\vec{k}^+$ is exactly twice as great as the orthogonal projection of the displacement vector onto $\vec{k}^-$ (see FIG. 12)). If for the orientation angle θ for example 45° were to be chosen, the two projections would be the same length, from which for $\alpha_{l,m}$ it follows that $$\alpha_{l,\pm 1} = \alpha_{l,\pm 2}$$

∀l and the matrix $\hat{A}$ would thus be singular.

2.4.2 Hexagon

Figure 13:
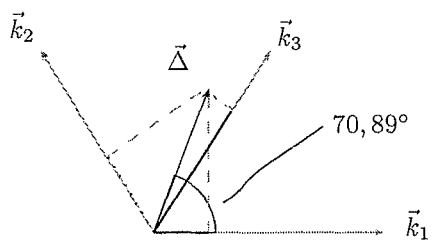
FIG. 13 shows the orthogonal projection of the displacement vector in the frequency space in the first order for a hexagonal illumination pattern.

For the hexagon the magic angle accordingly designates that explicitly ascertained direction for the displacement vector for which the orthogonal projection of the displacement vector onto $\vec{k}_2$ is exactly twice as great as the orthogonal projection onto $\vec{k}_1$. With (47) it follows from the fact that the orthogonal projection of the displacement vector onto $\vec{k}_3$ is exactly 3 times as great as the orthogonal projection onto $\vec{k}_1$ (see FIG. 13)).

2.5. The Other Magic Angles 2.5.1 N=13

By coherent laser excitation the case can occur that the 2nd harmonic orders of the hexagon in the picture are also recombined. In addition to the 3 first orders from equations (44)-(46) with the amount $$\frac{2\pi}{a},$$

for 3 further orders with the frequency $$|\vec{k}| = \sqrt{3}\frac{2\pi}{a}$$

according to equation (43) the following arises:

$$\vec{k}_{1,-3} = \frac{\pi}{a}\sqrt{3}\begin{pmatrix}1\\-\sqrt{3}\end{pmatrix} \approx \vec{k}_4 \quad (67)$$

$$\vec{k}_{1,3} = \frac{\pi}{a}\sqrt{3}\begin{pmatrix}1\\\sqrt{3}\end{pmatrix} \approx \vec{k}_5 \quad (68)$$

$$\vec{k}_{2,0} = \frac{2\pi}{a}\sqrt{3}\begin{pmatrix}1\\0\end{pmatrix} \approx \vec{k}_6 \quad (69)$$

The following applies $$\vec{k}_4 = \vec{k}_2 - \vec{k}_1 \quad (70)$$

$$\vec{k}_5 = \vec{k}_1 + \vec{k}_3 \quad (71)$$

$$\vec{k}_6 = \vec{k}_2 + \vec{k}_3 = \vec{k}_4 + \vec{k}_5 \quad (70)$$

or $$\vec{k}_2 = \vec{k}_1 + \vec{k}_4 \quad (73)$$

$$\vec{k}_5 = 2\vec{k}_1 + \vec{k}_4 \quad (74)$$

$$\vec{k}_5 = 3\vec{k}_1 + \vec{k}_4 \quad (75)$$

$$\vec{k}_6 = 3\vec{k}_1 + 2\vec{k}_4 \quad (76)$$

A total of 6 orders are recombined, therefore 2·6+1=13 measurements are necessary. For the sake of a clearer formulation, the vectors $\vec{k}_1$ and $\vec{k}_4$ are viewed as the basis, instead of $\vec{k}_1$ and $\vec{k}_2$, as in Section 2.3.

Analogously to the preceding solutions, again we examine the phase displacements $\alpha_{l,m}$ for $\vec{k}_1$ and $\vec{k}_4$:

$$\alpha_{l,\pm 1} = (l-1)\Delta\frac{2\pi}{a}\cos(\theta_{\pm 1}) \bigg|_{\pm\delta\Phi_1 = \pm\vec{k}_1 \circ \vec{\Delta}} \quad (77)$$

$$\alpha_{l,\pm 4} = (l-1)\frac{\Delta\frac{2\pi}{a}\cos(\theta_{\pm 4})}{\kappa\cdot\delta\Phi_1 = \kappa\cdot(\pm\vec{k}_1)\circ\vec{\Delta} = \pm\vec{k}_4\circ\vec{\Delta}} \quad (78)$$

$$= \kappa\Delta\frac{2\pi}{a}\cos(\theta_{\pm 1})$$

$\theta_{\pm 1}$ and $\theta_{\pm 4}$ designating the angle between $\vec{\Delta}$ and $\vec{k}_{\pm 1}$ or $\vec{k}_{\pm 4}$. From (73)-(76) the following is obtained:

$$\alpha_{l,\pm 2} = \pm(l-1)(\vec{k}_1 + \vec{k}_4)\circ\vec{\Delta} = \pm(l-1)(1+\kappa)^*\cdot\delta\Phi_1 \quad (79)$$

$$\alpha_{l,\pm 3} = \pm(l-1)(2\vec{k}_1 + \vec{k}_4)\circ\vec{\Delta} = \pm(l-1)(2+\kappa)^*\cdot\delta\Phi_1 \quad (80)$$

$$\alpha_{l,\pm 5} = \pm(l-1)(3\vec{k}_1 + \vec{k}_4)\circ\vec{\Delta} = \pm(l-1)(3+\kappa)^*\cdot\delta\Phi_1 \quad (81)$$

$$\alpha_{l,\pm 6} = \pm(l-1)(3\vec{k}_1 + 2\vec{k}_4)\circ\vec{\Delta} = \pm(l-1)(3+2\kappa)^*\cdot\delta\Phi_1 \quad (82)$$

Equations (77)-(78) lead geometrically to $$\frac{2\pi}{a}\Delta_y = \delta\Phi_1 \quad (83)$$

$$\frac{\pi}{a}(\Delta_x - \sqrt{3}\Delta_y) = \kappa\delta\Phi_1$$

$$\Leftrightarrow \quad (84)$$

$$\boxed{\Delta_x = \frac{a}{2\pi\sqrt{3}}(3+2\kappa)\delta\Phi_1 \\ \Delta_y = \frac{a}{2\pi}\delta\Phi_1} \quad (85)$$

$$\Leftrightarrow \quad (86)$$

$$\boxed{\tan\theta = \frac{\Delta_y}{\Delta_x} = \frac{\sqrt{3}}{3+2\kappa}} \quad (87)$$

As above, there are again 2 possible values for $\kappa$ and ultimately for $\hat{A}$ to obtain a unitary matrix:

$$\kappa_1 = 2 \quad (88)$$

$$\kappa_2 = 8 \quad (89)$$

Thus $$\boxed{\theta_1 = \arctan\left(\frac{\sqrt{3}}{7}\right) \approx 13.898°} \quad (90)$$

and $$\theta_2 = \arctan\frac{\sqrt{3}}{19}$$

$$\approx 5.20°.$$

For the pertinent angle $\gamma_l = \theta_l - 90°$ between $\vec{\Delta}$ and $\vec{k}_1$ there arise $\gamma_1 \approx -76.102°$ and $\gamma_2 \approx -84.8°$.

For $\kappa_1=2$ altogether for $\alpha_{l,m}$ the following is obtained:

$$\alpha_{l,m} = \frac{2\pi}{13}\delta\Phi_0 \begin{pmatrix} 0 & 0 & 0 & 0 & 0 & 0 & 0 & 0 & 0 & 0 & 0 & 0 & 0 \\ 0 & 1 & 12 & 3 & 10 & 4 & 9 & 2 & 11 & 5 & 8 & 7 & 6 \\ 0 & 2 & 11 & 6 & 7 & 8 & 5 & 4 & 9 & 10 & 3 & 1 & 12 \\ 0 & 3 & 10 & 9 & 4 & 12 & 1 & 6 & 7 & 2 & 11 & 8 & 5 \\ 0 & 4 & 9 & 12 & 1 & 3 & 10 & 8 & 5 & 7 & 6 & 2 & 11 \\ 0 & 5 & 8 & 2 & 11 & 7 & 6 & 10 & 3 & 12 & 1 & 9 & 4 \\ 0 & 6 & 7 & 5 & 8 & 11 & 2 & 12 & 1 & 4 & 9 & 3 & 10 \\ 0 & 7 & 6 & 8 & 5 & 2 & 11 & 1 & 12 & 9 & 4 & 10 & 3 \\ 0 & 8 & 5 & 11 & 2 & 6 & 7 & 3 & 10 & 1 & 12 & 4 & 9 \\ 0 & 9 & 4 & 1 & 12 & 10 & 3 & 5 & 8 & 6 & 7 & 11 & 2 \\ 0 & 10 & 3 & 4 & 9 & 1 & 12 & 7 & 6 & 11 & 2 & 5 & 8 \\ 0 & 11 & 2 & 7 & 6 & 5 & 8 & 9 & 4 & 3 & 10 & 12 & 1 \\ 0 & 12 & 1 & 10 & 3 & 9 & 4 & 11 & 2 & 8 & 5 & 6 & 7 \end{pmatrix} \quad (91)$$

and accordingly $\hat{A}_{l,m}=\exp(-i\alpha_{l,m})$ in this case again is a unitary matrix.

By an orientation of the hexagon pattern according to the angle $\theta$ and recording of 13 phase pictures with a phase displacement of $$\frac{2\pi}{13}$$

from one picture to the next, both the first and also the 2nd orders of the hexagon can be separated from one another.

Figure 14:
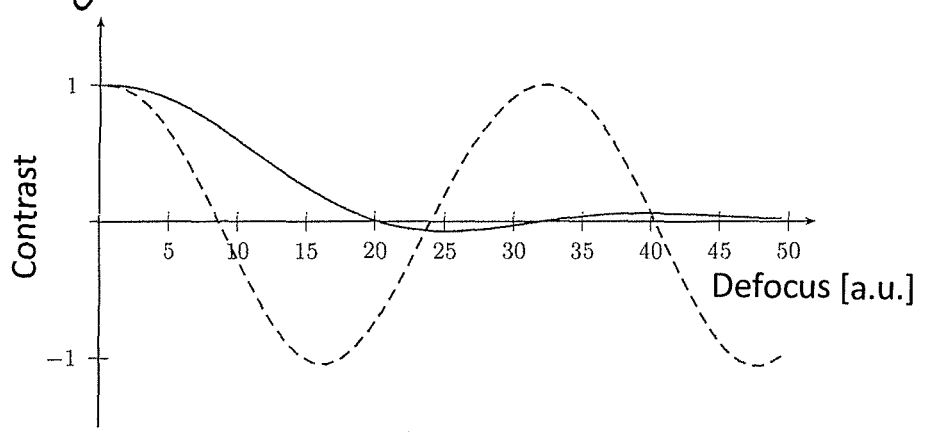
FIG. 14 shows a first curve (solid line) which represents the characteristic of a theoretical intensity-point spread function of the maximum in the axial direction which corresponds roughly to the incoherent contrast characteristic of a hexagonal pattern (with a period of roughly $\lambda/NA$) in the direction of the defocus, and a second curve (broken line) which represents this contrast in the z-direction assuming coherent illumination.
Figure 15:
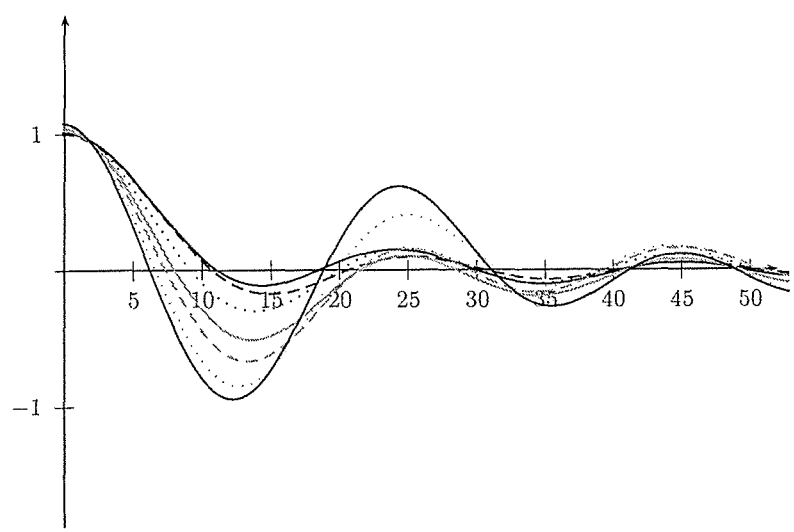
FIG. 15 shows a gradual transition between the two curves from FIG. 14, the theoretical contrast characteristics in the z-direction (when imaging a periodic structure) for different three-dimensional coherence lengths or different relative pupil stimulation between 24% and 100% (intermediate values: 29.4%, 38.5%, 45%, 56%, 70%) is shown.

These considerations are relevant mainly to the coherent case. In this case, from the coherence of the periodically structured excitation a narrowed PSF in the axial direction arises, as shown in FIG. 14). For partially coherent light (as can be easily produced for example by a coherence diaphragm), similarly a narrowed (structure) focus arises in the z direction. For partial illumination of the microscope objective a partial coherence arises, as is shown in FIG. 15).

The narrowing of the focus when using coherent light only occurs if the structure frequency $\tilde{v}$ used is greater than roughly 0.7. The minimum of the PSF half-value width in the z-direction is always $\tilde{v}=1$ (regardless of the degree of coherence).

2.5.2 N=19

If the frequency vectors with $$|\vec{k}| = 2*\frac{2\pi}{a}$$

are also examined $$\vec{k}_7 := \vec{k}_{0,4} = 2\vec{k}_1 \quad (92)$$

$$\vec{k}_8 := \vec{k}_{2,-2} = 2\vec{k}_2 \quad (93)$$

$$\vec{k}_9 := \vec{k}_{2,2} = 2\vec{k}_3 \quad (94)$$

it is apparent that altogether 19 phase pictures are necessary for a solution (with a relative phase displacement of $$\frac{2\pi}{19}).$$

Analogously to the aforementioned method it is also possible here to construct a unitary matrix. As possible values for $\kappa$ the following is obtained $$\kappa_1 = 6 \quad (95)$$

$$\kappa_2 = 10 \quad (96)$$

The pertinent values for $\theta$ follow from equation (87):

$$\theta_1 = 6.59° \quad (97)$$

$$\theta_2 = 4.31° \quad (98)$$

2.5.3 Other Solutions

For the use of nonlinear superresolution with structured illumination under certain circumstances it would be necessary to consider still higher orders of the hexagon (for a corresponding number of phase pictures taken) in the computation. Up to a value of N=43 unitary matrices and thus optimum theoretical solutions were found.

TABLE 1

Summary of all possible solutions for the hexagon with pertinent values for N and the respective magic angles.

| n | 1 | 2 | 3 | 4 | 5 | 6 |
|---|---|---|---|---|---|---|
| N | 7 | 13 | 19 | 31 | 37 | 43 |
| $\kappa_1$ | 1 | 2 | 6 | 4 | 9 | 5 |
| $\kappa_2$ | 5 | 8 | 10 | 24 | 25 | 35 |
| $\|\vec{k}\|/\frac{2\pi}{a}$ | 1 | $\sqrt{3}$ | 2 | $\sqrt{7}$ | 3 | $2\sqrt{3}$ |
| $\theta_1$ [°] | 19.11 | 13.90 | 6.59 | 8.95 | 4.72 | 7.59 |
| $\theta_2$ [°] | 7.59 | 5.21 | 4.31 | 1.95 | 1.87 | 1.36 |

3. Noise

As already indicated in part (2.1), the average error (or more accurately the average value of the variance of the error) in an evaluation with a unitary matrix $$\hat{A}_{m,l} \approx \frac{1}{\sqrt{N}}e^{-i\frac{2\pi}{N}ml}$$

is invariant:

$$\langle|\delta I_s^{(m)}|^2\rangle = \left\langle \sum_{l,n} \hat{A}_{m,l}^{-1}\delta I_l(\hat{A}_{m,n}^*)^{-1}\delta I_n \right\rangle = \quad (99)$$

$$= \frac{1}{N}\left\langle \sum_{l,n} e^{i\frac{2\pi}{N}m(l-n)}\delta I_l \delta I_n \right\rangle = \frac{1}{N}N\langle\delta(I_l)^2\rangle \quad (100)$$

$$= \langle|\delta I_l|^2\rangle \quad (101)$$

In order to look into equation (100), it can be considered that the sum on the left side on average will yield only contributions with l=n, since the measurement errors on different raw pictures are not correlated.

Compared to equation (10), it is apparent that a certain modulation in the raw picture for this choice of $\hat{A}$ amplified by a factor $\sqrt{N}$:

$$\hat{A}^{-1}\begin{pmatrix} I_1(\vec{x}) \\ I_2(\vec{x}) \\ \vdots \\ I_M(\vec{x}) \end{pmatrix} = \sqrt{N} \begin{pmatrix} I_0(\vec{x}) \\ \frac{1}{2}I_s^{(1)}(\vec{x})e^{-i\Phi_1(\vec{x})} \\ \frac{1}{2}I_s^{(-1)}(\vec{x})e^{+i\Phi_1(\vec{x})} \\ \frac{1}{2}I_s^{(2)}(\vec{x})e^{+i\Phi_2(\vec{x})} \\ \vdots \\ \frac{1}{2}I_s^{(-n)}(\vec{x})e^{+i\Phi_n(\vec{x})} \end{pmatrix} \quad (102)$$

For the relative error in the evaluation therefore the following arises $$\frac{\langle |\delta I_s^{(m)}| \rangle}{I_s^{(m)}} = \frac{1}{\sqrt{N}} \frac{|\delta I_l|}{I_{in\text{-}focus}} \quad (103)$$

If possible orientation errors are to be considered, the condition number of the matrix is also included in the error $$\frac{\langle |\delta I_s^{(m)}| \rangle}{I_s^{(m)}} = cond(\hat{A}) \frac{1}{\sqrt{N}} \frac{|\delta I_l|}{I_{in\text{-}focus}}$$

If it is assumed that the input error $|\delta I_l|$ is Poisson-distributed, overall for the relative error in the evaluation the following is obtained $$\frac{\langle |\delta I_s^{(m)}| \rangle}{I_s^{(m)}} = cond(\hat{A}) \sqrt{\frac{\gamma}{NK\Phi_{in\text{-}focus}\tau}} \quad (104)$$

Here $\gamma$ is the detector gain, K the contrast of the structure in the sample which has been achieved (depending on the detected out-of-focus portion), $\Phi_{in\text{-}focus}$ is the photons emitted per unit of time from the in-focus and r is the total exposure time for a raw picture.

It is apparent that the number of computed raw pictures has no effect on the duration of an acquisition. If the errors of any two methods which use the different values $N_1$ and $N_2$ ($N_2 > N_1$) for the evaluation are compared, it is apparent that the method with $N_2$ pictures for a choice of $$\tau_2 = \tau_1^{\frac{N_1}{N_2}}$$

has the same evaluation error as the method which computes only $N_1$ pictures.

For the rate of acquisition the number of phase pictures taken is therefore not directly decisive. In any case it should be watched that the value for N is in no case set to be so large than the signal strength on an individual phase picture approaches the read noise of the camera.

the camera is still able to read out a complete picture within r

For the method described in part (2.2) and (2.3) with chessboard and hexagon, for any evaluation in the case of the chessboard there are 2, for the hexagon 3 independent sections or quasi-confocal pictures.

for comparison: When using a grating and evaluating for example 7 raw pictures, a quasiconfocal picture is obtained which an error smaller by $$\sqrt{\frac{3}{7}}$$

[sic] than if 3 raw pictures with the same exposure time had been computed. In any case when using equations (60)-(63) only one solution for (60) (a nonconfocal picture) and (61) (a quasi-confocal picture) is obtained. The other solutions yield (if only the 1st order are [sic] contained in the picture of the grating) 0 or an average error.

By averaging over several sections for the chessboard or hexagon the relative error is reduced again $$\frac{\langle |\delta I_s^{(m)}| \rangle}{I_s^{(m)}} = \begin{cases} cond(\hat{A}) \sqrt{\dfrac{\gamma}{2NK\Phi_{in\text{-}focus}\tau}} & \text{Chessboard} \\ cond(\hat{A}) \sqrt{\dfrac{\gamma}{3NK\Phi_{in\text{-}focus}\tau}} & \text{Hexagon} \end{cases} \quad (105)$$

If it is still considered that for the hexagon based on the filling factor contrast values stronger by up to 1.28 times can be achieved, (compare Section (2.3.1)), especially for the hexagon $$\frac{\langle |\delta I_s^{(m)}| \rangle}{I_s^{(m)}} \approx cond(\hat{A}) \sqrt{\frac{\gamma}{4.91 NK\Phi_{in\text{-}focus}\tau}} \quad (106)$$

$$\approx \frac{1}{2.2} cond(\hat{A}) \sqrt{\frac{\gamma}{NK\Phi_{in\text{-}focus}\tau}}$$

an error one to 2 times smaller is obtained. Theoretically therefore a quasiconfocal structured illumination with a hexagon compared to the grating should yield the same signal-to-noise in the evaluation at a quarter of the exposure time.

We claim as follows:

1. A method of operating a microscope device comprising:
providing a microscope device with an objective, a light source for illuminating a sample over an illumination beam path, an arrangement for producing a flat illumination pattern which is structured in two directions on the sample, a surface detector for detecting light coming from the sample over one picture beam path, an arrangement for shifting the illumination pattern on the sample in one displacement direction, and a control unit, the method further including taking one picture at a time of the light detected by the detector as a phase picture in different positions of the pattern along the displacement direction and computationally reconstructing from these phase pictures an overall Structured Illumination Microscopy (SIM) picture of the illuminated sample region, characterized in that the displacement direction is oblique to the main axes of symmetry of the illumination pattern and depending on the illumination pattern is chosen such that the number of phase pictures which is necessary for the reconstruction of the SIM picture corresponds to the theoretically minimally required value for the number of Fourier orders of the illumination pattern used in the computational reconstruction.

2. The method of claim 1, wherein the illumination pattern is a hexagonal point pattern and the displacement direction is chosen to be in the range from 1 to 20 degrees relative to one of the three main axes of symmetry, and at least 7 phase pictures is the minimally required value.

3. The method of claim 2, wherein the displacement direction is chosen to be in the range from 4 to 20 degrees relative to one of the three main axes of symmetry.

4. The method of claim 1, wherein the arrangement for producing the illumination pattern is made in order illuminate all regions of the sample surface which is to be illuminated at the same time with the illumination pattern for each phase picture.

5. The method of claim 1, wherein the arrangement for producing the illumination pattern is made in order to sequentially assemble and again disassemble the illumination pattern in partial regions of the sample surface which is to be illuminated for each phase picture, the partial regions altogether covering the sample surface which is to be illuminated so that the sample surface which is to be illuminated is not simultaneously, but sequentially partially illuminated with the illumination pattern, the control unit controlling the detector such that essentially only a corresponding region of the detector is active at the time on which the just illuminated partial region of the sample surface is imaged.

6. A method of operating a microscope device comprising:
providing a microscope device including an objective, a light source for illuminating a sample over an illumination beam path, an arrangement for producing a structured illumination microscopy (SIM) illumination pattern which is structured in at least one direction of space on the sample, a surface detector for detecting light coming from the sample over one picture beam path, an arrangement for shifting the illumination pattern on the sample in one displacement direction, and a control unit, the method further including taking one picture at a time of the light detected by the detector as a phase picture in different positions of the pattern along the displacement direction, an overall picture of the illuminated sample region being computationally reconstructed from the phase pictures, the arrangement for producing the illumination pattern sequentially assembling and again disassembling the illumination pattern for each phase picture in partial regions of the sample surface which is to be illuminated, the partial regions altogether covering the sample surface which is to be illuminated so that the sample surface which is to be illuminated is not simultaneously, but sequentially partially illuminated with the illumination pattern, and the control unit controlling the detector such that essentially only a corresponding region of the detector is active at the time on which the just illuminated partial region of the sample surface is imaged, and characterized in that the displacement direction is oblique to the main axes of symmetry of the illumination pattern and depending on the illumination pattern is chosen such that the number of phase pictures which is necessary for the reconstruction of the SIM picture corresponds to the theoretically minimally required value for the number of Fourier orders of the illumination pattern used in the computational reconstruction.

7. The method of claim 6, wherein the arrangement for producing the illumination pattern assembles and disassembles the illumination pattern in the form of a strip which migrates in one direction.

8. The method of claim 7, wherein the width of the strip is chosen such that the sample region which is illuminated with it is imaged onto at least three detector lines.

9. The method of claim 7, wherein the strip is structured only in the longitudinal direction.

10. The method of claim 7, wherein the strip is diffraction-limited in the transverse direction.

11. The method of claim 7, wherein the arrangement for producing the illumination pattern is allows the strip to migrate only in the direction transversely to the strip.

12. The method of claim 7, wherein the arrangement for producing the structured illumination pattern has a cylindrical lens array, the direction of the migrating strip being parallel to the axial direction of the cylindrical lenses.

13. The method of claim 7, wherein the imaging of the strip on the detector in the longitudinal direction of the strip extends only over a partial region of the detector surface, the arrangement for producing the illumination pattern allowing the strip to migrate when the pattern is being assembled not only in the direction transversely to the strip, but also in the direction lengthwise to the strip in order to follow a curved trajectory.

14. The method of claim 7, wherein the displacement direction of the illumination pattern contains one component in the longitudinal direction of the strip.

15. The method of claim 7, wherein the arrangement for producing the structured illumination pattern produces the illumination pattern in the object plane or a plane which is conjugated to the object plane.

16. The of claim 15, wherein the arrangement for producing the structured illumination pattern produces the illumination pattern by means of interfering focal points of coherent illumination light in the pupil of the objective.

17. The method of claim 16, wherein the arrangement for shifting the illumination pattern on the sample causes a relative phase shift of the amplitudes of the focal points in the pupil of the objective in order to shift the illumination pattern on the sample.

18. The method of claim 17, wherein the arrangement for shifting the illumination pattern on the sample has a galvanometric scanner in or near the pupil, an acousto-optical modulator or an interferometer with a combination of piezo-actuator and mirror in one arm of the interferometer in order to cause the relative phase shift of the focal points in the pupil of the objective.

19. The method of claim 15, wherein the arrangement for producing the structured illumination pattern has an element for producing a point pattern in one intermediate picture plane.

20. The method of claim 19, wherein the element for producing the point pattern in the intermediate picture plane is a perforated mask which is located in the intermediate picture plane.

21. The method of claim 19, wherein the element for producing the point pattern in the intermediate picture plane is a microlens array which is located between the light source and the intermediate picture plane in order to produce focal points of the illumination light in the intermediate picture plane.

22. The method of claim 19, wherein the arrangement for shifting the illumination pattern on the sample has a beam deflection element in a noninfinite space between the intermediate picture plane (30) and a first tubular lens.

23. The method of claim 22, wherein the beam deflection element is made as motorized deflection mirror or as rotary glass window.

24. The method of claim 19, wherein the arrangement for producing the illumination pattern has a scan device with one scan lens which moves illumination light over the element for producing the point pattern in the intermediate picture plane when sequentially assembling and disassembling the illumination pattern.

25. The method of claim 19, wherein the microscope device is made such that the surface detector is located in a plane which is absolutely symmetrical to the intermediate picture plane with the point pattern.

26. The method of claim 25, wherein the intermediate picture plane is imaged by means of a first tubular lens and the objective onto the sample, and the sample is imaged by means of the objective and a second tubular lens which is identical to the first tubular lens onto the surface detector, the illumination beam path being separated from the picture beam path by means of a color divider.

27. The method of claim 7, wherein the microscope device is made for detection of two-photon excitation of the sample.

\* \* \* \* \*